United States Patent
Chitalia et al.

(10) Patent No.: US 10,478,464 B2
(45) Date of Patent: Nov. 19, 2019

(54) COMPOSITIONS AND METHODS OF USE

(75) Inventors: Vipul C. Chitalia, Cambridge, MA (US); Daniel Prabakaran, Wayland, MA (US); Ajit Bharti, West Roxbury, MA (US); Gamini S. Jayatilake, Broomfield, CO (US); Xiong Fu, Superior, CO (US)

(73) Assignee: Kirit Shah, Portland, OR (US)

( * ) Notice: Subject to any disclaimer, the term of this patent is extended or adjusted under 35 U.S.C. 154(b) by 0 days.

(21) Appl. No.: 12/687,769

(22) Filed: Jan. 14, 2010

(65) Prior Publication Data

US 2010/0209543 A1 Aug. 19, 2010

Related U.S. Application Data

(60) Provisional application No. 61/205,144, filed on Jan. 14, 2009.

(51) Int. Cl.
*A61K 36/00* (2006.01)
*A61K 36/11* (2006.01)
*A61K 31/20* (2006.01)
*A61K 45/06* (2006.01)

(52) U.S. Cl.
CPC .............. *A61K 36/11* (2013.01); *A61K 31/20* (2013.01); *A61K 45/06* (2013.01)

(58) Field of Classification Search
CPC .... A61K 36/11; A61K 31/20; A61K 2300/00; A61P 35/00; A61P 35/02
See application file for complete search history.

(56) References Cited

FOREIGN PATENT DOCUMENTS

CN 101 301 407 A 11/2008

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Jain, RK. Science (1996); 271: 1079-1080.salt, prodrug, prodrug salt, solvate, hydrate, and polymorph thereof.*
Dermer, GD. Bio/Technology (1994); 12:320. Another anniversary for the war on cancer.*
Pathak et al, Protective potentials of a potentized homeopathic drug, Lycopodium-30, in ameliorating azo dye induced hepatocarcinogenesis in mice. Molecular and Cellular Biochemistry, (Apr. 2006) vol. 285, No. 1-2, pp. 121-131.*
Balick et al., "Lycopodium Spores used in Condom Manufacture: Associated Health Hazards," Economic Botany (1989), 43(3):373-377.
Pathak et al., "Protective potentials of a potentized homeopathic drug, Lycopodium-30, in ameliorating azo dye induced hepatocarcinogenesis in mice," Molecular and Cellular Biochemistry (2006), 285:121-131.
Sugai et al., "Both Enantiomers of 8-Hydroxy-hexadecanoic Acid Inhibit the Spore Germination of Lygodium japonicum," Agric. Biol. Chem. (1984), 48(8):2155-2156.
Sakai et al., "Amino Acid Sequence Study of Ferredoxin from a Club Moss, *Lycopodium clavatum* L.", Bot. Mag. Tokyo (1992), 105:71-82.
International Search Report issued in related application PCT/US2010/021046, dated Sep. 30, 2010.
Written Opinion issued in related application PCT/US2010/021046, dated Sep. 30, 2010.
Database WPI Week 200910; Thomson Scientific, London, GB; AN 2009-B37459 XP002679613.
Supplementary European Search Report of PCT/US2010/021046; EP 10 73 2090.
Chinese Patent Office Action dated Dec. 4, 2013 for corresponding CN Appln. 201080012006.0.

* cited by examiner

*Primary Examiner* — Qiuwen Mi

(57) ABSTRACT

This invention relates to the use of plant extracts, compositions thereof, and compounds isolated from plant extracts or obtained from synthetic means thereof, for the treatment of diseases, disorders or symptoms thereof (e.g., proliferation disorders, cancer).

5 Claims, 11 Drawing Sheets

Proton NMR Spectrum of 8-hydroxy-hexadecanoic acid (1) in CDCl₃

Carbon-13 NMR Spectrum (full range) of 8-hydroxy-hexadecanoic acid (1) in CDCl$_3$ Carbon-13 NMR Spectrum (Expansion) of 8-hydroxy-hexadecanoic acid (1) in CDCl$_3$ X : parts per Million : 13C ESI-MS (Negative Mode) of 8-Hydroxy-hexadecanoic Acid (1)

GC-MS of the Methyl Ester of 8-Hydroxy-hexadecanoic Acid (1)

Extract of *Lycopodium Clavatum* Induces PARP Cleavage (S)-8-HHA Inhibits HOP-92 Lung Cancer Cell Survival Effects of 8-HHA on Survival of Liver Cancer Cell Lines (S)-8-HHA decreases Survival of PLC-5 Liver Cancer Cell Lines (S)-8-HHA Induces PARP Cleavage in SNU and PLC-5 Cancer Cell Lines (S)-8-HHA Reduces the Protein Levels of FAS Receptor in PCL-5 Cancer Cell Lines 8-HHA reduces Tumor Growth in PLC-5 Liver Cancer Cells 8-HHA Reduces Tumor Growth in HOP-92 Lung Cancer Cells

COMPOSITIONS AND METHODS OF USE

TECHNICAL FIELD OF THE INVENTION

This invention relates to plant extract compositions, isolated active agents, and methods of use for the treatment of cancer.

The identification of new extracts and compounds for therapeutic use is of continuing biomedical importance and natural products continue to garner attention for this endeavor. Proliferation disorders continue to provide challenges to the health of humans and animals and treatment regimens for such disorders remain as an unmet need across a broad spectrum. Because of the variation of mechanisms, signaling processes, and targets involved in proliferation disorders, identification of new and more efficacious compositions, compounds and methods of treatment is of great interest to the medical community as well as the public at large.

*Lycopodium clavatum*, also known as Wolf's Foot and Club Moss Lycopodiaceae, belongs to genus *Lycopodium* and family Lycopodiaceae. It derives its name as wolf's foot as the branch tips resemble a wolf's paws (lukos means wolf and podos means foot). The plant is ubiquitiously found in subtropical and tropical forests in the world. The sporophyte produces spores within sporangia after meiosis. In *Lycopodium* the sporangia are clustered into cone-like strobili in which each sporangium is protected by a leaf-like sporophyll. The extract from the spores of the plant was fractionated to yield isolated extracts and compounds in the search for new and interesting compositions having novel therapeutic activity.

SUMMARY OF THE INVENTION

This invention relates to the method of using a plant extract herein to treat a proliferation disorder in a subject. One aspect of this invention the method of using an isolated compound from a plant extract herein to treat a proliferation disorder in a subject. In one embodiment, the proliferation disorder is a cancer. Certain embodiments provide that the cancer is a leukemia, lung cancer, liver cancer, or colon cancer. In one embodiment, the cancer is a non-small cell lung cancer. In another embodiment, the cancer is a liver cancer.

In one embodiment, the compound is 8-hydroxy-palmitic acid ("8-HHA"), or a salt, prodrug, prodrug salt, solvate, hydrate, and polymorph thereof. In another embodiment, the compound used in accordance with the methods of this invention is a racemic mixture of R- and S-enantiomers of 8-hydroxy-palmitic acid. In one embodiment, the compound is the S-enantiomer of 8-hydroxy-palmitic acid ("(S)-8-HHA"). In another embodiment, the compound is the R-enantiomer of 8-hydroxy-palmitic acid ("(R)-8-HHA").

Another aspect of this invention is a composition comprising a plant extract herein (e.g., extract of *Lycopodium clavatum*). Another aspect is a composition comprising an isolated compound from a plant extract herein. Another aspect is a composition comprising an isolated compound from a plant extract herein having one or more substituent(s).

Another aspect is a compound (or combinations of compounds) delineated herein (or methods using the compounds/combinations delineated herein) wherein the compound or compound combinations are demonstrated to possess anticancer activity in a subject (e.g., animal model, mouse, rat, rabbit, primate, human). Examples herein are instructive for representative methods to determine such effect.

In one embodiment, the compound (or combinations of compounds) delineated herein is obtained from a procedure comprising extraction from a plant. In certain embodiments, the procedure for use in obtaining the compound (or combinations of compounds) further includes any of isolation, evaporation, and partitioning steps of the plant extracts.

In another embodiment, the compound (or combinations of compounds) delineated herein is obtained from a synthetic means.

Another aspect of this invention is a pharmaceutical composition comprising a plant extract herein (e.g., BCP-21 extracts, any of BCP-21 extract fractions in Tables 1 or 2) or a compound (e.g., 8-hydroxyhexadecanoic acid, any of BCP compounds 1-10 herein) that occurs in a plant extract herein (e.g., BCP-21 extracts, any of BCP-21 extract fractions in Tables 1 or 2). In one embodiment, the pharmaceutical composition comprises a racemic mixture of 8-HHA, or a salt, prodrug, prodrug salt, solvate, hydrate, and polymorph thereof. In one embodiment, the pharmaceutical composition comprises the S-enantiomer of 8-hydroxy-palmitic acid ("(S)-8-HHA") in a substantial enantiomeric purity. In another embodiment, the pharmaceutical composition comprises the R-enantiomer of 8-hydroxy-palmitic acid ("(R)-8-HHA") in a substantial enantiomeric purity.

In another aspect, such compositions can be included in a kit.

The above compositions (and method of treatment delineated herein) may be further combined with appropriate chemo- and biotherapeutic agents. Examples of such agents include but are not limited to Aldesleukin, Alemtuzumab, Alitretinoin, Altretamine, Aminolevulinic acid, Anagrelide, Anastrozole, Arsenic trioxide, Asparaginase, Bacille Calmette-Guérin (BCG), Betamethasone, Bexarotene, Bicalutamide, Bleomycin, Busulfan, Capecitabine, Carboplatin, Carmustine, Chlorambucil, Chromic phosphate P-32, Cisplatin, Cladribine, Conjugated estrogens, Cortisone, Cyclophosphamide, Cytarabine liposome, Cytarabine, ara-, Dacarbazine, Dactinomycin, actinomycin D, Daunorubicin, Daunorubicin citrate liposome, Denileukin diftitox, Dexamethasone, Diclofenac, Docetaxel, Doxorubicin, Doxorubicin liposome, Epirubicin, Esterified estrogens, Estradiol, Estradiol valerate, Estramustine, Estrone, Ethinyl estradiol, Etoposide, Etoposide phosphate, Exemestane, Floxuridine, Fludarabine phosphate, Fluorouracil, Fluorouracil, Fluorouracil, Fluoxymesterone, Flutamide, Gemcitabine, Gemtuzumab ozogamicin, Goserelin acetate, Granisetron, Hydrocortisone, Hydroxyprogesterone, Hydroxyurea, Ibritumomab tiuxetan, Idarubicin, Ifosfamide, Imatinib mesylate, Interferon alfa-2a, Interferon alfa-2b, Irinotecan, Letrozole, Leuprolide acetate, Levothyroxine, Lomustine, Mechlorethamine, Medroxyprogesterone, Medroxyprogesterone, Megestrol acetate, Melphalan, Mercaptopurine, Methotrexate sodium, Methoxsalen, Methylprednisolone, Methyltestosterone, Metyrosine, Mitomycin, mitomycin-c, Mitotane, Mitoxantrone, Nandrolone phenpropionate, Nilutamide, Octreotide acetate, Oprelvekin, Oxymetholone, Pegaspargase, Pentostatin, Plicamycin, Polifeprosan 20/carmustine, Porfimer sodium, Prednisolone, Prednisone, Procarbazine, Progesterone, Rituximab, Samarium-153 lexidronam pentasodium, Sodium iodide I-131, Sodium phosphate P-32, Streptozocin, Strontium-89 chloride, Talc, Tamoxifen citrate, Temozolomide, Teniposide, Testolactone, Testosterone enanthate, Thioguanine, Thiotepa, Topotecan, Toremifene citrate, Trastuzumab, Tretinoin, Triamcinolone, Triptorelin pamoate, Valrubicin, Vinblastine, Vincristine and Vinorelbine.

In yet another aspect, the invention provides the use of a compound of any of the formulae herein, alone or together with one or more additional therapeutic agents in the manufacture of a medicament, either as a single composition or as separate dosage forms, for treatment or prevention in a subject of a disease, disorder or symptom set forth herein. Another aspect of the invention is a compound of the formulae herein (isolated natural or synthetic) for use in the treatment or prevention in a subject of a disease, disorder or symptom thereof delineated herein.

DETAILED DESCRIPTION OF THE INVENTION

Definitions

Figure 1:
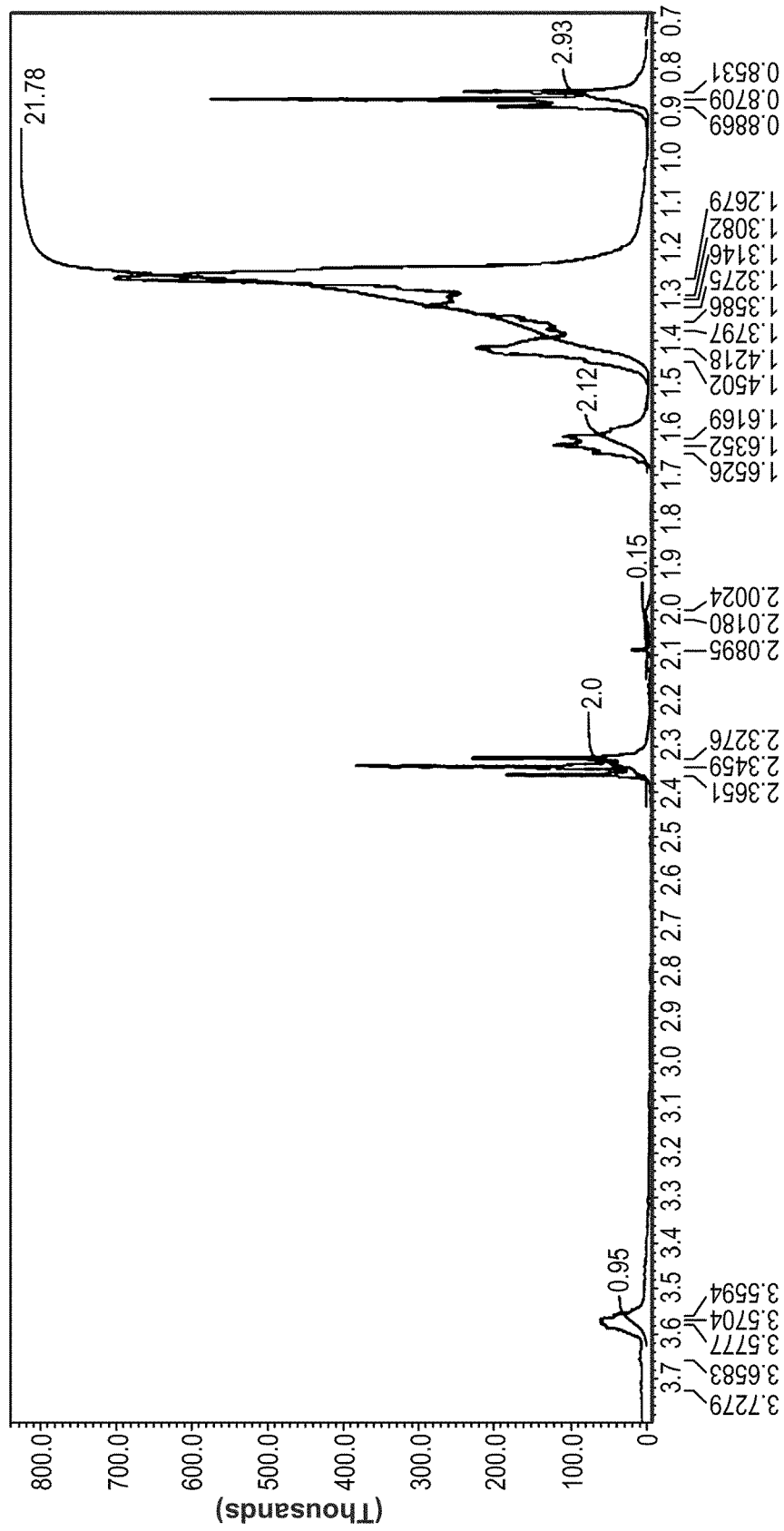
FIG. 1-FIG. 3 are NMR spectra of a compound isolated from BCP-21 extract.
Figure 2:
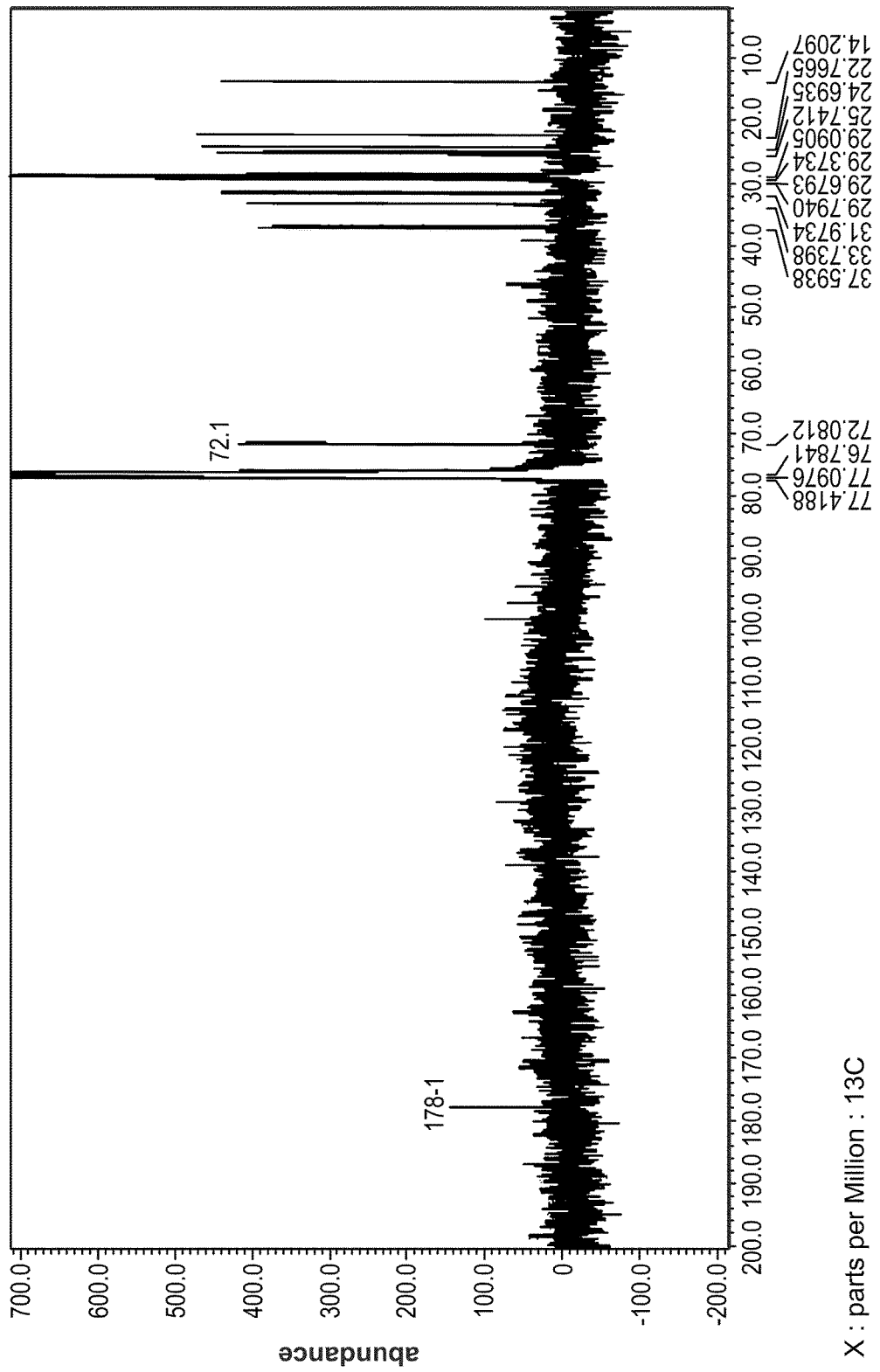
Figure 3:
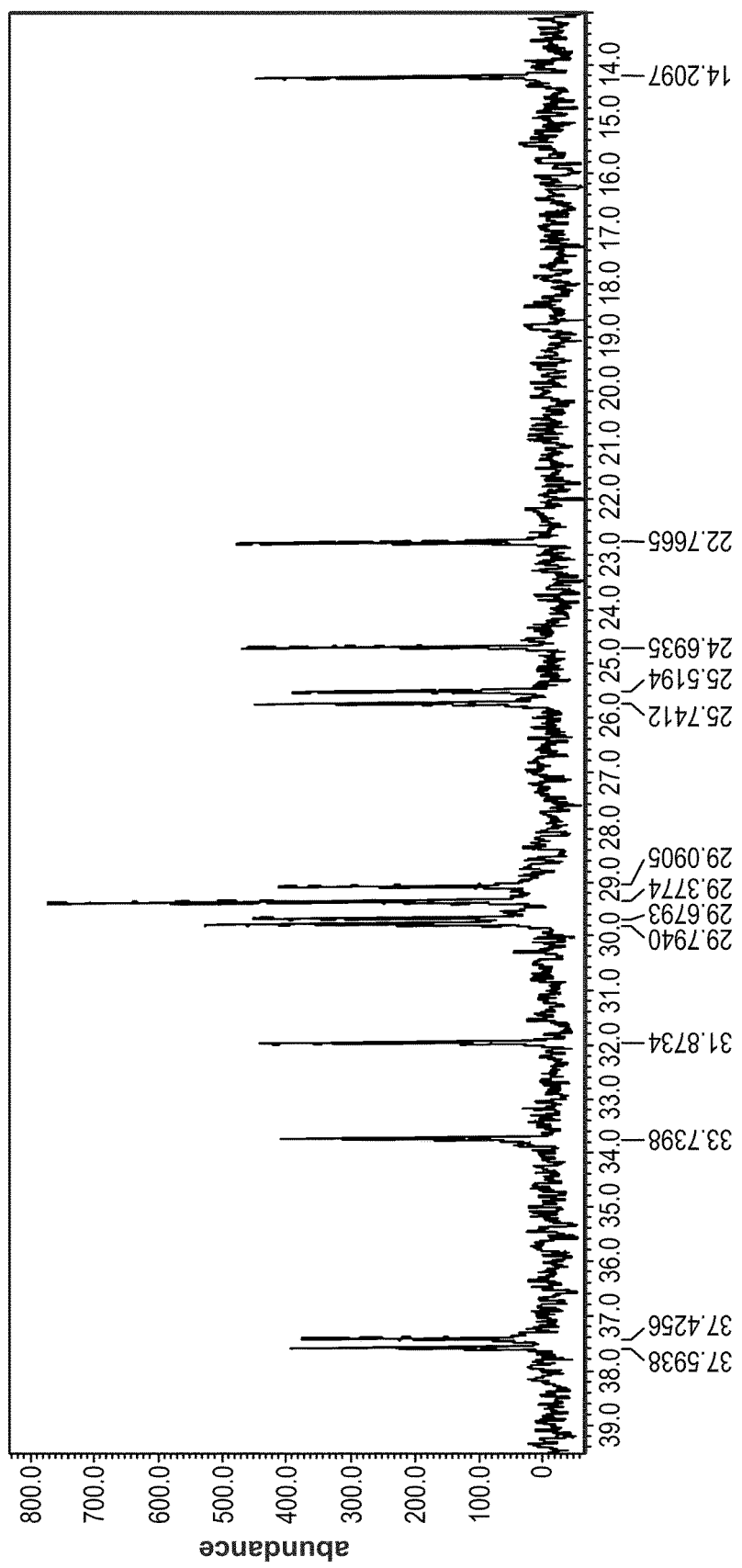
Figure 4:
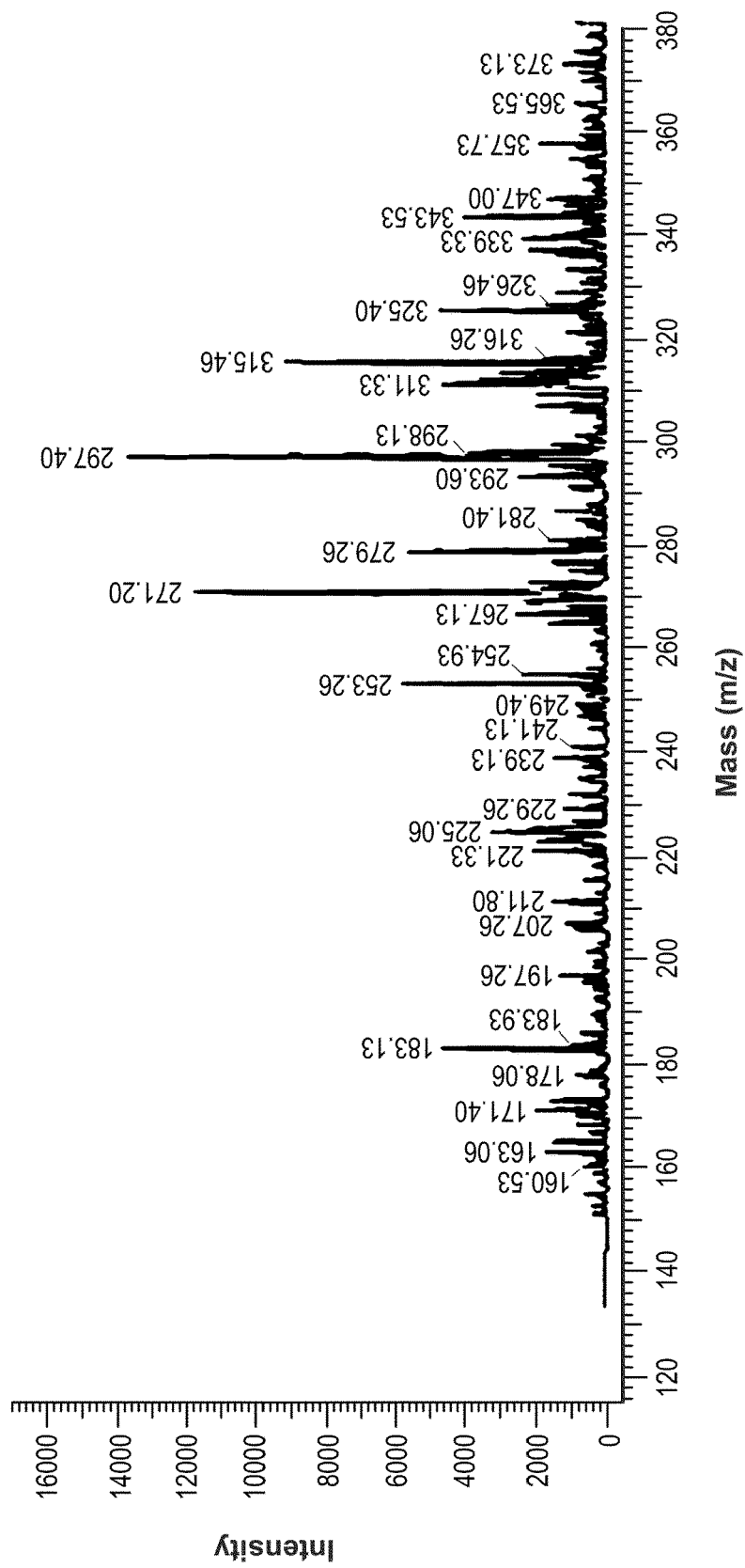
FIG. 4-FIG. 5 are MS spectra of a compound isolated from BCP-21 extract.
Figure 5:
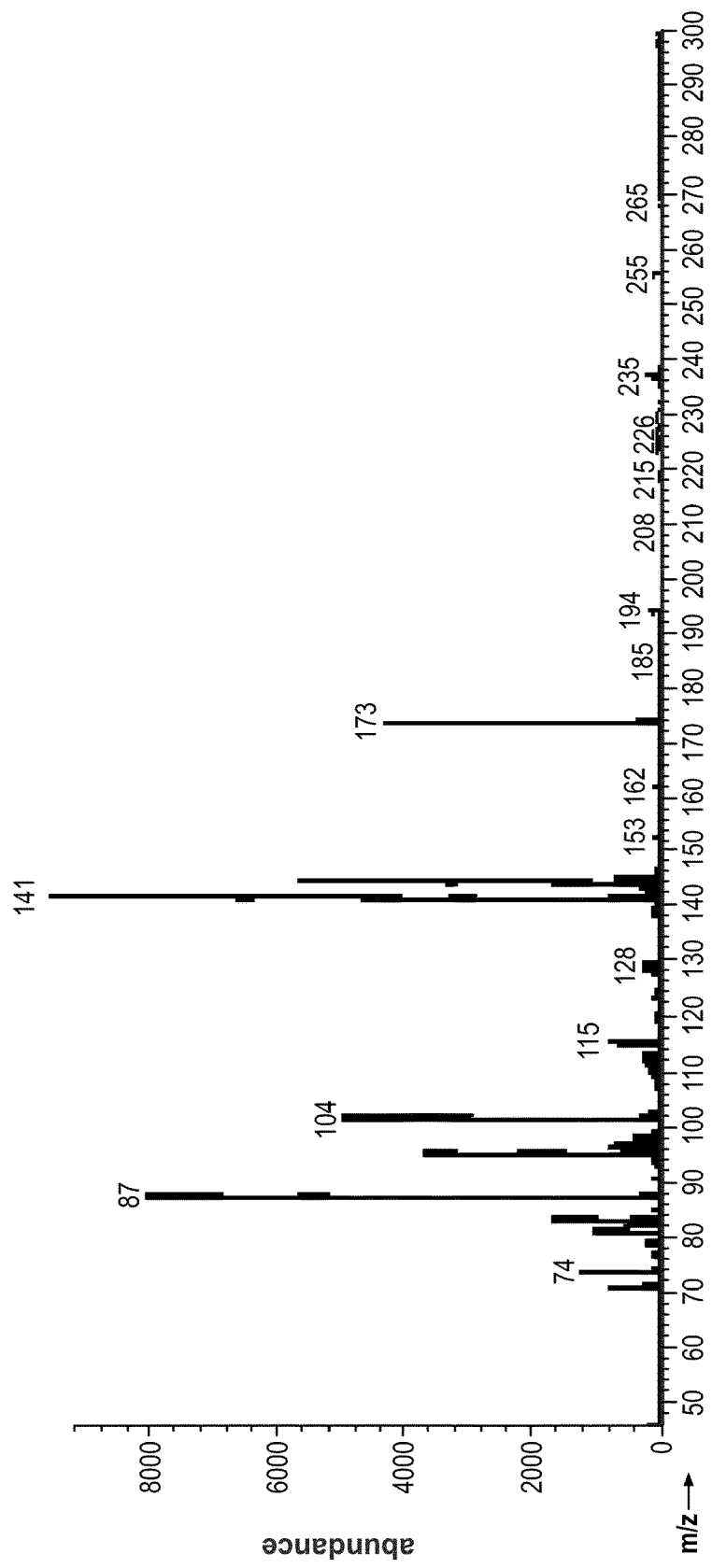

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder. For example, any protein or polynucleotide having an alteration in expression level or activity that is associated with a disease or disorder.

The term "cancers" generally refers to a class of diseases in which a group of cells display uncontrolled growth (division beyond the normal limits), invasion (intrusion on and destruction of adjacent tissues) and sometimes metastasis (spread to other locations in body). Examples of cancers include, but are not limited to, leukemia, lung cancers, liver cancers, colon cancers, melanoma, breast cancers, CNS cancers, ovarian cancers, renal cancers, and prostate cancers. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The compounds herein can also be utilized in compound forms including salts, prodrugs, and prodrug salts, solvates, hydrates, and polymorphs of a compound of a formulae herein.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate) analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development;

Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive). The term "arylalkyl" refers to a moiety in which an alkyl hydrogen atom is replaced by an aryl group. The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —$(CH_2)_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH═CH—CH═CH—, —$CH_2$—CH═CH—, —$CH_2$—CH═CH—$CH_2$—, —$C(CH_3)_2$CH═CH— and —CH($C_2H_5$)—CH═CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —$CH(CH_3)$—C≡C— and —C≡C—$CH(C_2H_5)CH_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbons. The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. In aspects, functional group delineated herein, e.g., alkyl, alkenyl, alkynyl, cycloalkyl, cycloalkenyl, aryl, heterocyclyl, or heteroaryl, can be substituted with a substituent (e.g., those listed below). Suitable substituents include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where n is independently 0-6 inclusive. Each $R^{15}$ is independently hydrogen, $C_1$-$C_4$ alkyl or $C_3$-$C_6$ cycloalkyl. Each $R^{16}$ is independently hydrogen, alkenyl, alkynyl, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, $NH_2$, $C_1$-$C_4$ alkylamino, $C_1$-$C_4$ dialkylamino, $C_1$-$C_2$ perfluoroalkyl, $C_1$-$C_2$ perfluoroalkoxy, or 1,2-methylenedioxy.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention.

The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

Other approaches to synthesizing compounds of the formulae herein can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, R, R', X, etc.) or not. The suitability of a chemical group in a compound structure for use in synthesis of another compound structure is within the knowledge of one of ordinary skill in the art. Additional methods of synthesizing compounds herein and their synthetic precursors, including those within routes not explicitly shown in schemes herein, are within the means of chemists of ordinary skill in the art. Methods for optimizing reaction conditions, if necessary minimizing competing by-products, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compounds herein, or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). A useful formulation for the compounds of this invention is the form of enteric pellets of which the enteric layer comprises hydroxypropylmethylcellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. A *Textbook of Drug Design and Development;* 2 ed.; Overseas Publ.: Amsterdam, 1996; pp 351-385; Pitman, I. H. *Medicinal Research Reviews* 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include other kinase inhibitors and/or other chemotherapeutic agents for the treatment of the diseases and disorders discussed above.

Such agents are described in detail in the art. Preferably, the second therapeutic agent is an agent useful in the treatment or prevention of a disease or condition selected from cancer.

Even more preferably the second therapeutic agent co-formulated with a compound of this invention is an agent useful in the treatment of kinase-mediated disease/disorders such as cancer, immune disorders, cardiovascular disease, viral infection, inflammation, metabolism/endocrine disorders and neurological disorders.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to one aspect, the invention provides a method of treating a subject suffering from or susceptible to a disease or disorder or symptom thereof (e.g., those delineated herein) comprising the step of administering to said subject an effective amount of a compound (e.g., an isolated compound; a compound herein) or a composition of this invention. Such diseases are well known in the art and are also disclosed herein.

The methods can further comprise that wherein the composition is an extract of *Lycopodium clavatum* (e.g., BCP-21 extracts, any of BCP-21 extract fractions in Tables 1 or 2) or an isolated compound (e.g., 8-hydroxyhexadecanoic acid (8-HHA), any of BCP compounds 1-10 herein) that occurs in a plant extract herein (e.g., BCP-21 extracts, any of BCP-21 extract fractions in Tables 1 or 2).

In one embodiment of this invention the isolated compound is 8-hydroxyhexadecanoic acid ("8-HHA"), or a salt, prodrug, prodrug salt, solvate, hydrate, and polymorph thereof. Certain embodiments provide that the compound is a racemic mixture of R- and S-enantiomers of 8-hydroxy-palmitic acid. In one embodiment, the compound is the S-enantiomer of 8-hydroxy-palmitic acid ("(S)-8-HHA"). In another embodiment, the compound is the R-enantiomer of 8-hydroxy-palmitic acid ("(R)-8-HHA").

In another embodiment, the compound (or compositions) used in the methods of this invention is obtained through a synthetic means.

In one aspect of this invention the disease or disorder is a caspase mediated disease or disorder.

In one aspect of this invention the disease or disorder is mediated by caspase-3 mediated cell death.

In one aspect of this invention the disease or disorder is a caspase-3 mediated disease or disorder.

In one aspect of this invention the disease or disorder is treated by inducing cell death.

In one aspect of this invention the disease or disorder is treated by inducing cell death mediated by caspase-3.

In one aspect of this invention the disease or disorder can be modulated by caspase-3.

In one aspect, the method of treating involves treatment of a disorder that is a proliferation disorder or symptom thereof. These include cancer, tumors, any disease wherein a neoplastic agent is appropriate.

Examples of cancers which the present compounds, compositions and methods of treatment can be used to treat include cancer (e.g., leukemia, liver cancer, lung cancer, colon cancer, CNS cancer, melanoma, renal cancer, and caspase-3 mediated cancers), allergic and inflammatory disorders. A human or animal patient suffering from a proliferation disorder, e.g., cancer, may thus be treated by a method comprising the administration thereto of a compound of the present invention as defined above. The condition of the patient may thereby be improved or ameliorated.

Diseases and conditions treatable according to the methods of this invention include, but are not limited to, cancer and inflammatory disorders. Cancers which can be treated according to the methods of this invention include, but are not limited to liver, hepatocellular, leukemia, lung, colon, CNS, melanoma, renal, etc.

One embodiment provides that the cancer treatable according to the methods of this invention is is a leukemia, lung cancer, liver cancer, or colon cancer. In one embodiment, the cancer is a liver cancer. Another embodiment provides that the cancer is a lung cancer. In one embodiment, the lung cancer is a non-small cell lung cancer. Certain instances provide that the cancer treatable according to the methods of this invention relates to HOP-92 mediated diseases (e.g., non-small cell lung cancers).

Yet in another embodiment, the cancer which can be treated according to the methods of this invention is a leukemia.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In one embodiment, the invention provides a method of modulating the activity of a caspase enzyme (e.g., caspase-3) in a cell comprising contacting a cell with one or more compounds of any of the formulae herein.

In another embodiment, the above method of treatment comprises the further step of co-administering to said patient one or more second therapeutic agents. The choice of second therapeutic agent may be made from any second therapeutic agent known to be useful for indications herein.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

Use of Compounds of this Invention

The present invention also provides kits for use to treat diseases, disorders, or symptoms thereof, including those delineated herein. These kits comprise: a) a pharmaceutical composition comprising one or more compounds of any of the formula herein (e.g., composition herein, any specific compound herein) or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein. The compounds/compositions can be administered sequentially or concurrently with radiation treatment administration.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprise information and/or instructions for the physician, pharmacist or subject. Such memory aids include numbers printed on each chamber or division containing a dosage that corresponds with the days of the regimen which the tablets or capsules so specified should be ingested or administered to a subject, or days of the week printed on each chamber or division, or a card which contains the same type of information. In one aspect, the instructions further relate to radiation administration to the subject.

In yet another aspect, this invention provides the use of a compound (or a combination of compounds) of the invention, alone or together with one or more additional therapeutic agents in the manufacture of a medicament, either as a single composition or as separate dosage forms, for treatment or prevention in a subject of a disease, disorder or symptom set forth herein. Another aspect of the invention is a compound (or a combination of compounds) of the invention for use in the treatment or prevention in a subject of a disease, disorder or symptom thereof delineated herein.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EXAMPLES

General Procedures

NMR spectra were acquired on a JEOL ECLIPSE 400 MHz NMR spectrometer referenced to the solvent used ($CDCl_3$). ESI-MS (negative mode) was obtained with Hitachi M-8000 mass spectrometer. Analysis was performed using an Agilent Model 5971A mass spectrometer (range: 70-550 amu) with a Phenomenex ZB-WAX-column (300 m×0.32 mm×0.25 m) and an Agilent Model 5890 gas chromatography.

HPLC Assay Method 1 (Reversed Phase Method): This gradient method can be used to assay the extract and column fractions. The column is a 4.6×100 mm, Phenomenex Luna (2), 3 μC18 column (PIN 00D-4251-EO). Flow rate 1.0 mL/min; Temp. 40° C., injection 10 uL. Detection is ELSD and UV at 200 nm. Normal-phase chromatography samples are evaporated and reconstituted in acetone before being injected.

HPLC Assay Method 2 (Normal Phase Method): This gradient method can be used to assay column fractions and final products. The column is a 4.6×250 mm, 5μ, Alltech, Adsorbosil Silica Column (P/N 298017). Mobile phases: Hexane/EtOAc, Flow rate 1.0 mL/min; Temp. 40° C., injection 10 uL. Detection is ELSD. Normal-phase chromatography samples can be injected directly, and solid sample are reconstituted in EtOAc before being injected. Acetone solution could give a broad or double peak.

Bioassay for apoptotic activity of HPLC fractions: One hundred thousand HeLa cells/well, were plated in 24 well cell culture plates. The cells were grown for 24 hours in cell culture incubator. After 24 hours the cells were treated with compounds derived from BCP21 purification. Fractions generated by HPLC during the purification were dried and re-suspended in DMSO. The cells were treated with three different concentrations of compounds in each fraction. The cells were harvested after 24 hours to determine the % apoptosis (cell death). The cells were treated with trypan blue to estimate the cell death. Cell death less than 10% was marked as + while 100% was represented by ++++, 50 and 75% were marked with ++ and +++ respectively.

Example 1

Extraction and Isolation from *Lycopodium Clavatum*

Isolation of BCP-21: Spores of *Lycopodium clavatum* are extracted using 95% ethanol. The resulting extractive phases are combined and may be stored as solutions in 95% ethanol or can be concentrated.

Evaporation and Partitioning of the Extract: BCP21 ethanol solution (1 L) was evaporated at 45° C. under vacuum to give a suspension which contained small amount of precipitate. 50 mL water was added to the suspension, and partitioned with 200 mL methylene chloride (MC). The MC layer was separated in a separatory funnel, and evaporated to dryness, giving 18.9 g of oily residue. The water layer was dried to give 2.84 g solids. HPLC profiles of the BCP21 ethanol extract and the MC soluble residue were done.

Example 2

40M Silica Biotage Fractionation

Since bioassays indicated that the aforementioned MC-soluble residue contained the active compounds, 5 g of this material was dissolved in 15 mL MC, and loaded onto a 40 M silica cartridge which had been equilibrated with 800 mL hexane. The column was eluted with 10% acetone/hexane (A/H) (1 L), 20% A/H (1 L), 25% A/H (1.2 L), and acetone (0.5 L). Based on bioassay results, F5 to F8, and F9 to F11 of the 25% A/H eluate were combined and dried by a stream of nitrogen to give 2615-182-8 (43.4 mg) and 2615-182-9 (36.3 mg), respectively. Table 1 details fraction sampling results guided by apoptotic assaying.

TABLE 1

Weights and Bioassay Results of the Fractions from 40M Column

| Sample # | Fraction | Weight (mg) | Sampling for Bioassay (mg) | Bioassay Result |
|---|---|---|---|---|
| 1 | 10% A/H F1 | 2980.8 | 78.6 | + |
| 2 | F2 | 601.2 | 53.6 | + |
| 3 | F3 | 39.8 | 10.8 | + |
| 4 | F4 | 32.4 | 5.4 | + |
| 5 | 20% A/H F1 | 87.0 | 12.4 | ++ |
| 6 | F2 | 110.6 | 13.7 | + |
| 7 | F3 | 62.1 | 6.4 | ++ |
| 8 | F4 | 193.2 | 35.5 | ++ |
| 9 | F5 | 93.2 | 18 | ++ |
| 10 | 25% A/H F1 | 14.4 | 5.2 | ++ |
| 11 | F2 | 14.3 | 2.9 | ++ |
| 12 | F3 | 19.1 | 3.0 | ++ |
| 13 | F4 | 15.9 | 3.1 | +++ |
| 14 | F5 | 13.9 | 2.4 | ++++ |
| 15 | F6 | 13.4 | 2.0 | ++++ |
| 16 | F7 | 13.3 | 1.7 | ++++ |
| 17 | F8 | 13.4 | 2.0 | ++++ |
| 18 | F9 | 14.1 | 1.5 | ++++ |
| 19 | F10 | 12.2 | 1.6 | ++++ |
| 20 | F11 | 10.2 | 2.0 | ++++ |
| 21 | Acetone F1 | 52.5 | 7.0 | +++ |
| 22 | F2 | 33.5 | 3.6 | + |

Example 3

12M Silica Biotage Fractionation

The aforementioned active pooled product 2615-182-8 (43.4 mg) was dissolved in 2 mL 30% EtOAc/hexane at 50° C. and the solution injected onto a 12 M Biotage silica cartridge equilibrated with 100 mL 30% EtOAc/hexane. The column was eluted with 60 mL of 35% EtOAc/hexane, 100 mL of 40% EtOAc/hexane, 60 mL of 45% EtOAc/hexane, 60 mL of 80% EtOAc/hexane yielding 26 fractions. 1 mL each was sent for bioassays after drying. The remaining solution of each fraction was dried to get the weights. Table 2 details fraction sampling results guided by apoptotic assaying.

TABLE 2

Weights and Bioassay Results of the Fractions from 12M Column

| Sample # | Fraction | Weight (mg) | Bioassay Result |
|---|---|---|---|
| 1 | 35% EtOAc/HexaneF1 | 2.5 | − |
| 2 | F2 | 0.14 | − |
| 3 | F3 | 0 | − |
| 4 | F4 | 0 | − |
| 5 | 40% EtOAc/HexaneF1 | 0.27 | − |
| 6 | F2 | 0.44 | ++ |
| 7 | F3 | 0.67 | ++ |
| 8 | F4 | 0.71 | +++ |
| 9 | F5 | 0.72 | +++ |
| 10 | F6 | 0.69 | +++ |
| 11 | F7 | 0.59 | +++ |
| 12 | F8 | 0.48 | +++ |
| 13 | F9 | 0.85 | ++ |
| 14 | F10 | 0.51 | ++ |
| 15 | 45% EtOAc/HexaneF1 | 0.67 | + |
| 16 | F2 | 0.44 | − |
| 17 | F3 | 0.63 | − |
| 18 | F4 | 0.82 | + |
| 19 | F5 | 0.64 | − |
| 20 | F6 | 0.45 | − |
| 21 | 80% EtOAc/HexaneF1 | 0.59 | − |
| 22 | F2 | 1.00 | + |
| 23 | F3 | 2.72 | +++ |
| 24 | F4 | 3.25 | +++ |
| 25 | F5 | 1.60 | +++ |
| 26 | F6 | 1.23 | +++ |

TABLE 3

BCP-Compound

| BCP-Compound | Table 2 Sample(s) |
|---|---|
| 1 | 1 |
| 2 | 3 |
| 3 | 7 |
| 4 | 13 |
| 5 | 14 |
| 6 | 18 |
| 7 | 22 |
| 8 | — |
| 9 | — |
| 10 | — |

Example 4

Preparation of Test Compound Samples for Assay

Preparation of the aforementioned compound fractions was performed according to that delineated in Table 4 as follows:

TABLE 4

| | Compound Preparation & Dilution | | |
|---|---|---|---|
| | 2% | 1% | 0.50% |
| BCP-Compound 1 | 80 μl of Compound 1 + 3920 ul of Media | 2000 ul of 2% Comp 1 + 2000 ul of Media | 2000 ul of 1% Comp 1 + 2000 ul of Media |
| BCP-Compound 2 | 80 μl of Compound 2 + 3920 ul of Media | 2000 ul of 2% Comp 2 + 2000 ul of Media | 2000 ul of 1% Comp 2 + 2000 ul of Media |
| BCP-Compound 3 | 80 μl of Compound 3 + 3920 ul of Media | 2000 ul of 2% Comp 3 + 2000 ul of Media | 2000 ul of 1% Comp 3 + 2000 ul of Media |
| BCP-Compound 4 | 80 μl of Compound 4 + 3920 ul of Media | 2000 ul of 2% Comp 4 + 2000 ul of Media | 2000 ul of 1% Comp 4 + 2000 ul of Media |

TABLE 4-continued

| | Compound Preparation & Dilution | | |
|---|---|---|---|
| | 2% | 1% | 0.50% |
| BCP-Compound 5 | 80 µl of Compound 5 + 3920 ul of Media | 2000 ul of 2% Comp 5 + 2000 ul of Media | 2000 ul of 1% Comp 5 + 2000 ul of Media |
| BCP-Compound 6 | 80 µl of Compound 6 + 3920 ul of Media | 2000 ul of 2% Comp 6 + 2000 ul of Media | 2000 ul of 1% Comp 6 + 2000 ul of Media |
| BCP-Compound 7 | 80 µl of Compound 7 + 3920 ul of Media | 2000 ul of 2% Comp 7 + 2000 ul of Media | 2000 ul of 1% Comp 7 + 2000 ul of Media |
| BCP-Compound 8 | 80 µl of Compound 8 + 3920 ul of Media | 2000 ul of 2% Comp 8 + 2000 ul of Media | 2000 ul of 1% Comp 8 + 2000 ul of Media |
| BCP-Compound 9 | 80 µl of Compound 9 + 3920 ul of Media | 2000 ul of 2% Comp 9 + 2000 ul of Media | 2000 ul of 1% Comp 9 + 2000 ul of Media |
| BCP-Compound 10 | 80 µl of Compound 10 + 3920 ul of Media | 2000 ul of 2% Comp 10 + 2000 ul of Media | 2000ul of 1% Comp 10 + 2000 ul of Media |
| BCP-DMSO | 80 ul of DMSO + 3920 ul of Media | 2000 ul of 2% DMSO + 2000 ul of Media | 2000 ul of 1% DMSO + 2000 ul of Media |

Example 5

Synthesis of Racemic 8-Hydroxypalmitic Acid ("8-HHA")

Synthetic Scheme for the Synthesis of Racemic 8-Hydroxypalmitic Acid

Synthetic route developed by Hauser

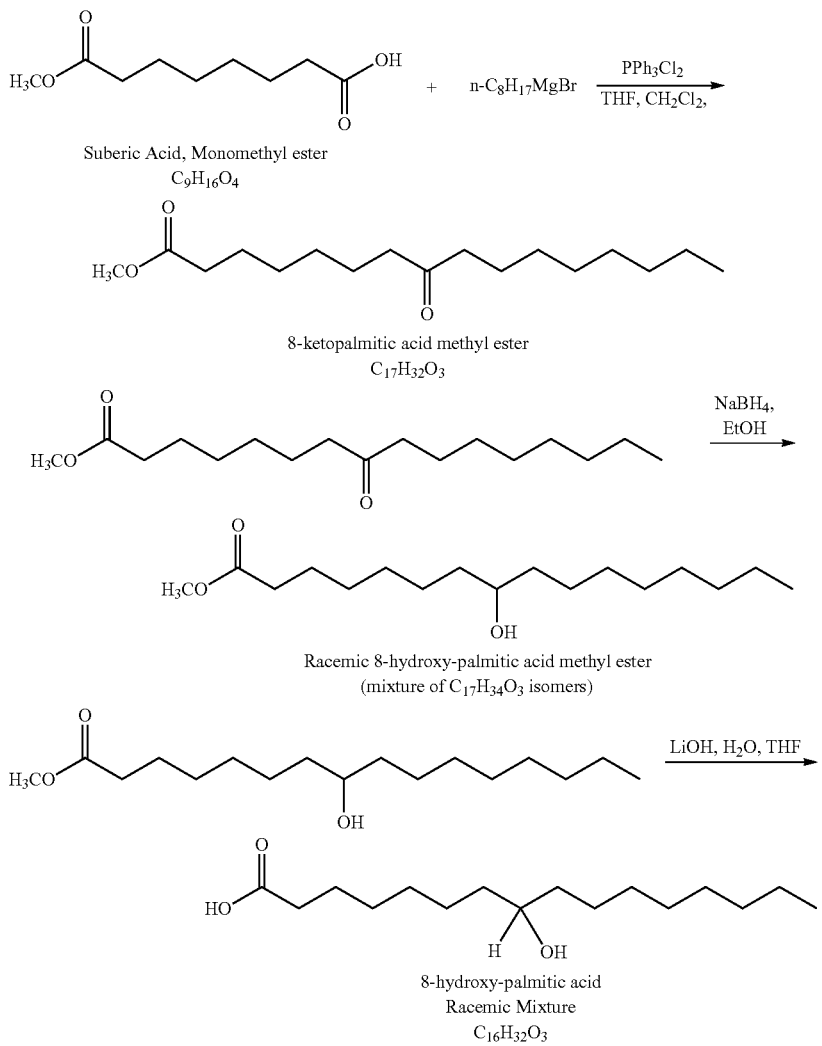

Two three necked flasks are equipped with gas inlet adaptor, septa and stir bars and then flasks were purged with Argon. Suberic acid monomethyl ester (10.0 g, 53.1 mmol, 1 equiv) was dissolved in THF (380 mL, 0.17M) in one flask. Triethylamine (0.95 mL, 64.1 mmol, 1.2 equiv) added gradually (over 4 min, using gas-tight syringe) and the mixture was stirred at room temperature for 1.25 h. A separate solution was made from PPh$_3$Cl$_2$ (24.4 g, 73.2 mmol, 1.4 equiv) in anhydrous DCM which is then cooled to <30° C. The suberic acid solution was added drop wise to the yellow PPh$_3$Cl$_2$ solution and stirred for 2 h at −35 to −20° C. The Grignard reagent was then added drop wise over 45 min while maintaining temperature −41 to −7° C. The reaction mixture stirred for 1.5 h, and then was quenched while still cold with 2N HCl (75 mL). After stirring for 20 min the yellow color fades. Thin later chromatography (silica gel 60, 25% acetone/hexanes) to give a reaction mixture as two major product spots plus PPh$_3$ and OPPh$_3$.

The reaction mixture was added to a separatory funnel along with ethyl acetate (200 mL) and 2N HCl (200 mL). The organic layer was collected and the aqueous layer was back-extracted with 2×80 mL ethyl acetate. The combined organic phases were neutralized by washing with NaHCO$_3$ (saturated solution, 2×90 mL), then washed with brine, (90 mL) dried over MgSO$_4$ (20 g, 30 min), filtered, rotoevaporated at 25° C. and dried under high vacuum for 3 h. To remove ethyl acetate the material is mixed with 20 mL DCM and re-evaporated to give 33 g of crude material.

The crude material is taken up in 1.0% acetone/DCM and loaded on a silica gel plug (240 mL) and flushed with 4 CV of 10% acetone/DCM. The first plug removed 10.4 g of OPPh$_3$ and a second removed 6.8 g of OPPh$_3$. Purification continued with flash column chromatography, in which a 5×29 cm column is packed with Silica gel 60 in 10% acetone/hexanes. The crude material was loaded in a minimum volume of 55% DCM/hexanes. Desired compound is eluted with 10% DCM/5% acetone/85% hexanes, Evaporation and drying of one fraction gives 2.7 g compound 1 (8-ketopalmitic acid methyl ester), and a repeat column on several impure fractions gave another 2.0 g compound 1. Overall yield 31% based on suberic acid mono methyl ester. Compound 1 (8-ketopalmitic acid methyl ester) was characterized by $^1$H NMR (in CDCl$_3$): 3.65 (s, 3H, OCH$_3$), 2.37. (m, 2H, O=CCH$_2$), 2.29 (t, 2H, O=CCH$_2$), 1.57 and 1.28, (br., 22H, CH$_2$), 0.87 (s, 3H, CH$_3$-terminal).

Compound 1 (2.86 g, 10.1 mmol) was dissolved in 50 mL ethanol and cooled in an ice bath. The sodium borohydride (1.9 g, 59.5 mmol) was added in portions at 1-17 C. The reaction was monitored by TLC (plates developed in 25% acetone/hexanes) where Rf was 0.56 for the ketone and 0.28 for the methyl ester. Additional portions of solid NaBH$_4$ were added over a 2 h period (total of 60 eq used) until no starting material was detected. The reaction was quenched by slowly adding 2N HCl (60 mL) to the cold solution, transferred to a separatory funnel and washed with DCM (3×35 mL). The combined organic layers were washed with NaHCO$_3$ (saturated, 35 mL) and brine (35 mL), then dried over MgSO$_4$ (7 g, 30 min) filtered and rotoevaporated to give a clear oil, which became a white waxy solid when stored at 4° C. (Yield 2.86 g).

The material was purified by flash chromatography (Silica gel 60, 20% acetone/heptane). After rotoevaporating to dryness the compound is an oil, and after drying on high vacuum the product is a white waxy solid. The $^1$H NMR spectra (CDCl$_3$) showed the predominant product as Compound 2 with small amounts of unknown impurities. Compound 2 (8-hydroxypalmitic acid methyl ester) was characterized by $^1$H NMR (in CDCl$_3$): 3.66 (s, 3H, OCH$_3$), (br, 1H, methine), 2.29 (t, 2H, O=CCH$_2$), 1.62 and 1.31, (br., 28H, CH$_2$), 0.87 (s, 3H, CH$_3$-terminal).

Compound 2 (1.97 g, 6.9 mmol) was dissolved in THF (28 mL). Lithium hydroxide was dissolved in water (Nanopure, 15 mL) and stirred 5 min. to dissolve. The LiOH solution was added slowly over 5 min to the ester solution and stirred at room temperature. The reaction was monitored by TLC (20% acetone/hexane) until the product disappeared and a new spot appeared at baseline (4 h). Work up involved rotoevaporating the reaction mixture to remove volatiles to get abundant white solids. The solids were rinsed with DCM, then combined with 2N HCl (solids mostly insoluble) and chloroform. The aqueous layer was extracted with CHCl$_3$ (3×75 mL)$^3$. Combined organic phases were dried with brine and MgSO$_4$ (30 min) then filtered, rotoevaporated and dried under high vacuum overnight to give 1.67 g of white solid as the final product (89% yield).

Analysis of the final product supported its identification as 8-hydroxy-palmitic acid, as the predominant product. $^1$H NMR (in CDCl$_3$): 5.5 (very broad, 1H, OH) (3.58 br, 1H, methine), 2.34 (t, 2H, O=CCH$_2$), 1.64 and 1.33, (br., 28H, CH$_2$), 0.87 (s, 3H, CH$_3$-terminal). $^{13}$C NMR (in CDCl$_3$): 178.40, 72.08, 37.59, 37.43, 33.79, 31.97, 29.79, 29.68, 29.37, 29.09, 25.73, 25.51, 24.69, 22.76, 14.20. LC-MS (ESI− mode in ACN—NH$_4$OH). Parent ion 271.13 m/z, theory: 272 (100%) 273 (17%). Melting point: 70.5° C.

Example 6

Synthesis of Both (S)- and (R)-8-Hydroxypalmitic Acid

Formation of R,S or racemic 1,2 epoxydecane from 1,2-decanediol

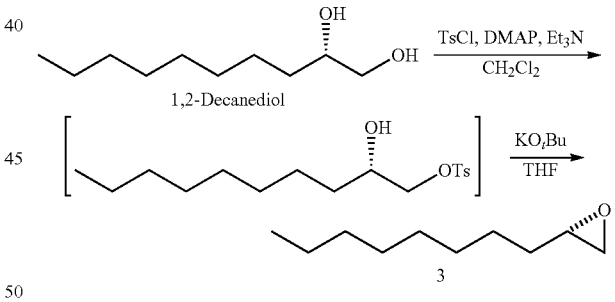

The reaction of racemic 1,2-decanediols with p-toluenesulfonyl chloride in the presence of base is known to give a mixture of the desired primary tosylate, bis-tosylate, and minor amounts of the secondary tosylate (*Bull. Korean Chem. Soc.* 2009 Vol. 30, No. 7, 1671-4). The generation of any secondary tosylate could adversely affect the stereochemical purity of the resulting epoxide due to inversion of the stereocenter during ring closure at the 2-position.

In this reaction, 23.9 ml (0.172 mol, 3.0 equiv.) of triethylamine in 10 ml of anhydrous dichloromethane was added slowly over a 40 minute period to a solution of 10.00 g (0.0574 mol) 1,2(S)-decanediol (99.5% "S"), 13.7 g (0.0717 mol, 1.25 equiv.) p-toluenesulfonyl chloride, 0.70 g (0.00574 mol, 0.10 equiv.), and 30 ml of anhydrous dichloromethane at <10° C. After stirring for 20 minutes at <10° C. the reaction was complete by TLC (100% CH$_2$Cl$_2$). After warming to room temperature, the product mixture was partitioned into the organic phase by the addition of 200 ml MTBE and 120 ml of 1 M HCl. The organic layer was washed 1×80 ml sat'd. NaHCO₃ solution, 1×80 ml water, and 1×80 ml sat'd. NaCl solution. Drying over sodium sulfate and concentration resulted in 21.7 g of residue that was carried directly on to the conversion to the epoxide. This residue was dissolved in 217 ml of anhydrous THF and 9.64 g (0.086 mol, 1.30 equiv.) of potassium t-butoxide was added at room temperature without cooling. After 30 minutes, the reaction was complete by TLC (10:1 heptane/ethyl acetate). The reaction was quenched by the addition of 100 ml water and the THF was removed in vacuo. The product mixture was partitioned into 300 ml MTBE and the aqueous layer back extracted 1×50 ml MTBE. The combined organics were then washed with 1×80 ml sat'd. NaCl solution. Drying over sodium sulfate and concentration resulted in 10.4 g of residue. The residue was short-path distilled and the 1,2(S)-epoxydecane was collected at ca. 60° C. and 1 mmg Hg. 6.11 g resulted for a 68% recovery with a GC-MS purity of >99%.

Reaction of Alkenylmagnesium Bromides with R,S or Racemic 1,2-Epoxydecane

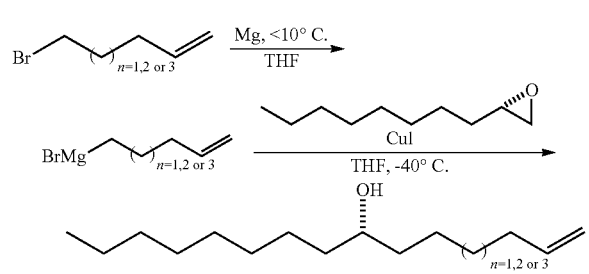

The formation of and addition of the Grignard reagents to racemic or chiral 1,-epoxydecane was performed according to a literature procedure (*J. Org. Chem.* 2009, 74, 5063-5066). The Grignards were prepared at ca. 0.5 M at <10° C. in order to minimize self-coupling products. No effort to titrate the Grignard reagents was made, and they were assumed to be 0.5 M. The addition of I₂ was not required in order to activate the magnesium turnings to get the Grignard reactions started.

To a dry 250 ml flask under N₂, charge 98 ml (0.049 mol, 1.5 equiv.) hept-6-enylmagnesium bromide ca. 0.5 M in THF (as prepared above). Cool the contents of the flask to −40° C. with stirring. Charge 1.24 g (0.00653 mol, 0.20 equiv.) of copper (I) iodide to the flask. After 0.5 hours at −40° C., slowly add a solution of 5.10 g (0.0326 mol) 1,2(S)-epoxydecane in 51 ml of anhydrous THF over at least 1 hour at −40±5° C. Continue to stir at −40° C. for 2 hours after the addition is complete after which the reaction is typically complete by TLC (40% EtOAc in heptane). After completion, 500 ml of MTBE, 125 ml of saturated ammonium chloride and 50 ml of water are added and mixed well for 15 minutes. Layers are cut and the organics are washed with 100 ml a mixture of 1 part saturated ammonium chloride and 1 part water. The organics are then washed 3×100 ml water, 1×50 ml saturated NaCl solution, dried over sodium sulfate, filtered, and concentrated to an oil which solidifies upon standing (8.6 g results). The product is chromatographed on 220 g of silica first eluting with 500 ml of heptane to remove any non-polar impurities, then with 10:1 (v:v) heptane/ethyl acetate. The product containing fractions are pooled and concentrated to give 8.11 g (97.6% yield) of 9(S)-hydroxyheptadec-1-ene as a waxy solid that is 96.7% pure by GC-MS.

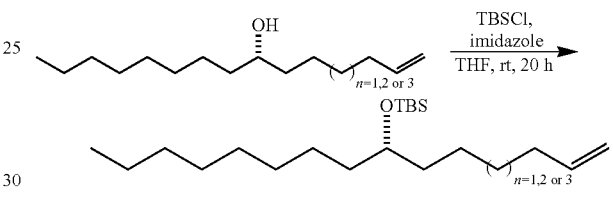

The protection of the alcohol was accomplished by the addition of 1.50 equiv. of t-butyldimethylsilyl chloride to a THF solution of the alkenols with 2.0 equiv. of imidazole as base. Typically, after 16-20 h at room temperature, the reaction was 92-96% complete. Additional TBS chloride and imidazole did not drive the reaction all the way to completion. Acidic aqueous work-up with partitioning into heptane allowed for the removal of imidazole without decomposition of the acid sensitive TBS protected alcohol. Flash chromatography with heptane on silica easily removed the residual unreacted alcohol and allowed the intermediates to be isolated with high purities (>99% by GC-MS) (NB 1362-42, 45, 86; 1341-89; 1380-15).

Ozonolysis/Pinnick Oxidation Route to the TBS Protected Acid

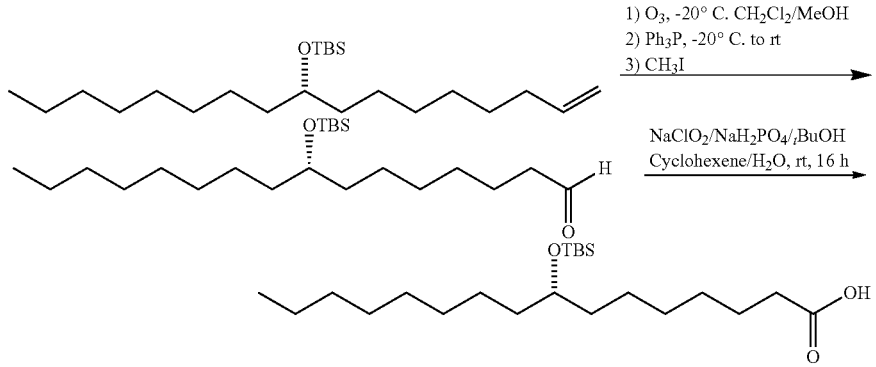

A solution of 9.83 g (0.0267 mol) of 9(S)-(t-butyldimethylsilyloxy)heptadec-1-ene, 0.10 g (0.00027 mol, 0.01 equiv.) Sudan red 7B in 138 ml of dichloromethane and 138 ml of methanol was treated with ozone at −25±5° C. Ozone addition was continued for another 6-7 minutes after the color of the indicator has discharged. The solution is then sparged with $N_2$ for at least 30 min. A solution of 13.99 g (0.0533 mol, 2.00 equiv.) of triphenylphosphine was then added over 4-5 minutes at <−15° C. and then allowed to warm to room temperature. After stirring for 30 minutes at room temperature the reaction is checked by GC-MS and checked again at 1.25 and 3 hours. All three checks typically indicate the same levels of triphenylphosphine, triphenylphosphine oxide, and product showing that the ozonide has been consumed. The reaction mixture is then concentrated to a pasty solid, and re-concentrated one time from 100 ml of dichloromethane (in order to remove methanol). The residue was then chromatographed on 300 g of silica eluting with heptane followed by 20:1 heptane/ethyl acetate. The product containing fraction are pooled and concentrated to give 13 g of oil that still contains 31% triphenylphosphine by GC-MS. The oil was re-chromatographed on 500 g of silica and the triphenylphosphine level was now 13%. This oil was dissolved in 100 ml of dichloromethane. 0.46 ml (0.0074 mol) of iodomethane was added and the mixture was stirred overnight after which all of the triphenylphosphine had been consumed (monitored by GC-MS). Finally, the product was flash chromatographed on 200 g of silica eluting with 10:1 heptane/ethyl acetate. After concentration, 8.00 g (89% yield) of 8(S)-(t-butyldimethylsilyloxy)hexadecanal was resulted with a GC-MS purity of 98.7%.

To a solution of 3.79 g (0.0102 mol) 8(S)-(t-butyldimethylsilyloxy)hexadecanal in 315 ml of t-butanol was added at room temperature over 30 minutes, a solution of 8.49 g (0.0939 mol, 9.17 equiv.) sodium chlorite and 8.50 g (0.0708 mol) sodium dihydrogenphosphate in 125 ml of water. The mild exotherm was controlled by a water bath. After stirring overnight, the reaction was complete by TLC (1:1:0.01 Heptane: EtOAc: HOAc). The t-butanol was removed in vacuo. The residue was dissolved in 200 ml water and 300 ml heptane and then 80 ml of 1.0 M HCl was added. The resulting heptane layer was washed 3×100 ml water, 1×75 ml saturated sodium chloride solution, dried over sodium sulfate, filtered and concentrated to give 3.79 g (95.7% yield) of 8(S)-(t-butyldimethylsilyloxy)hexadecanoic acid 99.4% purity by GC-MS (as the methyl ester from $TMSCHN_2$).

Removal of the TBS Protecting Group and Purification of 8(S)-Hydroxypalmitic Acid

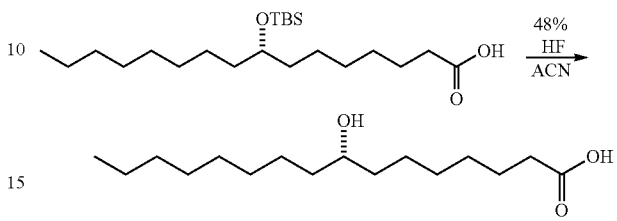

3.79 g (0.00980 mol) of 8(S)-(t-butyldimethylsilyloxy) hexadecanoic acid, 48 ml of ACN, and 2.13 ml (0.059 mol, 6 equiv.) of 48% hydrofluoric acid were combined and stirred for 1 hour. After 20-30 minutes the oily mixture becomes a suspension. After 1 hour, the starting material was completely consumed (as monitored by TLC (1:1:0.01 Heptane: EtOAc: HOAc)). Upon completion, 300 ml of MTBE and 300 ml of water were added and mixed thoroughly. The aqueous layer was removed and the organic layer washed 3×100 ml water, 1×100 ml saturated sodium chloride, dried over sodium sulfate, filtered and concentrated to give 2.50 g of solid. The solid was 95.6% ee at this point (NB 1380-51). The solid was dissolved in 40 ml of hot ACN and allowed to cool with stirring. The resulting suspension was cooled to <10° C. for 30 minutes, collected by filtration, washed with 20 ml cold ACN, and was dried under vacuum at 40° C. to give 2.18 g (82% yield) of 8(S)-hydroxypalmitic acid, that was >99% by GC-MS (as the methyl ester from $TMSCHN_2$) and 98.4% ee by HPLC-MS.

Mitsunobu Inversion to Give the 8(R) Enantiomer

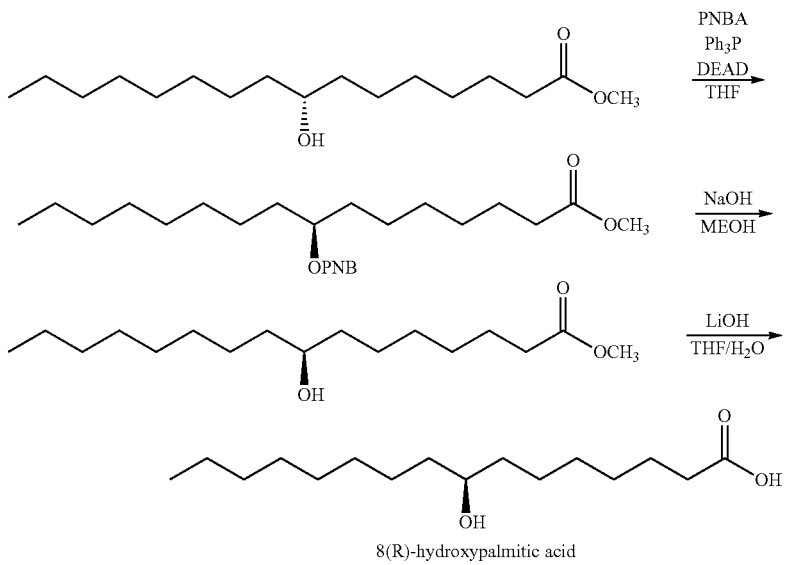

8(R)-hydroxypalmitic acid

To invert the stereo center of 8-hydroxyacid under Mitsunobu conditions, the carboxylic acid had to be protected as its methyl ester. Initially on small scale, diazomethane was used as a quick efficient method of conversion. Due to the dangerous nature of diazomethane, a safer alternative, TMS diazomethane, was used on the larger scale. 2.6 equivalents of TMS diazomethane were required to fully esterify the acid in MTBE/methanol. Attempts to invert the stereo center under Mitsunobu conditions using acetic acid proved less than ideal. The same conditions substituting 4-nitrobenzoic acid (*Organic Synthesis*, Collective Volume 9, page 607) provided the 8(R)-4-nitrobenzoate cleanly. Saponification using LiOH in THF/water followed by recrystallization from ACN provided the desired 8(R)-hydroxypalmitic acid that was 100% ee by HPLC-MS.

Example 7

General Assay Procedure for Determination of HeLa Cell Viability by Alamar Blue Assay Assessment of cell viability by alamar blue reduction method is routinely used for illustrating cytotoxic potential of candidate drugs. Alamar blue detects cell viability by utilizing a blue non-fluorescent dye resazurin, which is converted to a pink fluorescent dye, resorufin by cellular metabolic intermediates. The fluorescent signal generated from the assay is proportional to the number of living cells in the sample. Confluent HeLa cells (70-80%) grown in T-75 flasks were detached using trypsin-EDTA. Following centrifugation, the cells pellet was resuspended in DMEM medium and counted using a hemocytometer. Cells were seeded into 96 well plate at a density of 10,000 cells/100 µl/well and incubated at 37° C./5% $CO_2$ for 8 hrs. Media was removed and test compounds were added in the volume of 100 µl. The plate was incubated for 22, 46 & 70 hrs, after which 10 µl of alamar blue was added per well. At the end of 24, 48 & 72 hrs treatment with test compound, fluorescence was measured at 530 excitation and 590 nm emissions using a micro plate reader. Viability expressed as % control was plotted against drug concentration. Terfenadine was used as a reference compound in the protocol and showed a dose dependent inhibition in all the time points (24, 48 and 72 hrs) with reproducible IC50 values. Different compounds showed different viability.

Example 8

Data Analysis of Example 7 Assays

The mean value of duplicate wells was calculated. Viability of control cells was considered as 100% for all test concentrations. The percentage of cell viability of test samples was calculated as:

$$\% \text{ Viability} = 100 \times \frac{\text{Fluorescence Units of Test}}{\text{Fluorescence Units of Control}}$$

$IC_{50}$ values were determined by nonlinear regression analysis (curve fit) of percent viability data against drug concentration using the sigmoidal dose-response (variable) equation (Graph Pad Prism 4 software). BCP-6 and BCP-7 demonstrated particular effect on cells.

Quality Control:
The assay was evaluated for following quality checks:
i. $IC_{50}$ Value of Reference Compound: $IC_{50}$ value of Terfenadine
ii. % Coefficient of Variance between Replicates: The % CV between replicates was within the acceptable limits (10%).

Example 9

Preparation of Test Compound Samples. Preparation of the aforementioned compound fractions was performed according to that delineated in Table 5.

TABLE 5

| Compound Preparation & Dilution | | | |
|---|---|---|---|
| BCP-21 cmpd | 2% | 1.00% | 0.50% |
| Compound 1 | 40 µl of Compound 1 + 1960 ul of Media | 1000 ul of 2% Comp 1 + 1000 ul of Media | 1000ul of 1% Comp 1 + 1000 ul of Media |
| Compound 2 | 40 µl of Compound 2 + 3920 ul of Media | 1000 ul of 2% Comp 2 + 1000 ul of Media | 1000 ul of 1% Comp 2 + 1000 ul of Media |
| Compound 4 | 40 µl of Compound 3 + 3920 ul of Media | 1000 ul of 2% Comp 3 + 1000 ul of Media | 1000 ul of 1% Comp 3 + 1000 ul of Media |
| Compound 4 | 40 µl of Compound 4 + 3920 ul of Media | 1000 ul of 2% Comp 4 + 1000 ul of Media | 1000 ul of 1% Comp 4 + 1000 ul of Media |
| Compound 5 | 40 µl of Compound 5 + 3920 ul of Media | 1000 ul of 2% Comp 5 + 1000 ul of Media | 1000 ul of 1% Comp 5 + 1000 ul of Media |
| Compound 6 | 40 µl of Compound 6 + 3920 ul of Media | 1000 ul of 2% Comp 6 + 1000 ul of Media | 1000 ul of 1% Comp 6 + 1000 ul of Media |
| Compound 7 | 40 µl of Compound 7 + 3920 ul of Media | 1000 ul of 2% Comp 7 + 1000 ul of Media | 1000 ul of 1% Comp 7 + 1000 ul of Media |
| Compound 8 | 40 µl of Compound 8 + 3920 ul of Media | 1000 ul of 2% Comp 8 + 1000 ul of Media | 1000 ul of 1% Comp 8 + 1000 ul of Media |
| Compound 9 | 40 µl of Compound 9 + 3920 ul of Media | 1000 ul of 2% Comp 9 + 1000 ul of Media | 1000 ul of 1% Comp 9 + 1000 ul of Media |
| Compound 10 | 40 µl of Compound 10 + 3920 ul of Media | 1000 ul of 2% Comp 10 + 1000 ul of Media | 1000 ul of 1% Comp 10 + 1000 ul of Media |
| DMSO | 40 ul of DMSO + 3920 ul of Media | 1000 ul of 2% DMSO + 1000 ul of Media | 1000 ul of 1% DMSO + 1000 ul of Media |

Example 10

General Assay Procedure for Determination of Caspase-3 Activity on HepG2 Cells Cells that are suspected or have been induced to undergo apoptosis are first lysed to collect their intracellular contents. In our test system, lysates from cells treated with staurosporin were tested for protease activity by the addition of a caspase-specific peptide that is conjugated to the fluorescent reporter molecule 7-amino-4-methyl coumarin (AMC). The cleavage of the peptide by the caspase releases a fluorochrome that, when excited at 380 nm wavelength, emits fluorescence at 460 nm. The level of caspase enzymatic activity in the cell lysate is directly proportional to the fluorescence signal detected with a fluorescent microplate reader. Confluent HepG2 cells (70-80%) grown in T-75 flasks were detached using trypsin-EDTA. Following centrifugation, the cells pellet was resuspended in DMEM medium and counted using a hemocytometer. Cells were seeded into 96 well Plate at a density of 40,000 cells/100 µl/well and incubated at 37° C./5% $CO_2$ for 8 hrs. Media was removed and test compounds were added in the volume of 100 µl. After 30 min of pre treatment as above, 50 µL of 3× conc. of Staurosporine (final concentration of 20 µM) or 50 µL of medium (untreated control) was added to respective wells. After inducing with Staurosporine for 16 h. cells were lysed by addition of 50 µl of lysis buffer followed by 30 min incubation. After complete lysis as observed under microscope 100 µl of chilled buffer (assay buffer) was added to each well. Next DEVD-AMC (substrate, final Conc. 15 uM) was added and allowed the reaction to continue for 2 hrs. The fluorescence was measured by exciting at 380 nM and capturing the emission at 460 nM using BMG Polarstar fluorescent micro plate reader.

Example 11

Data Analysis of Example 10 Assays

Average the replicate Relative Fluorescence Value (RFU) for each standards, blanks and samples. Enzyme activity of control (staurosporine treated without inhibitor) was considered as 100% activity (0% inhibition). Fluorescence values (RFU) of Test/Reference compounds are compared against this for calculating % inhibition. The percentage inhibition of Test/Reference compound was calculated as follows:

$$\% \text{ Activity} = 100 \times \frac{RFU \text{ of Test/Reference compound}}{RFU \text{ of Control}}$$

$$\% \text{ Inhibition} = 100 - \% \text{ Activity}$$

$IC_{50}$ values were determined by nonlinear regression analysis (curve fit) of percent viability data against drug concentration using the sigmoidal dose-response (variable) equation (Graph Pad Prism 4 software). BCP-6 and BCP-7 demonstrated particular effect on caspase-3 inhibition.

Quality Control:
The assay was evaluated for following quality checks:
(i) $IC_{50}$ Value of Reference Compound: $IC_{50}$ value of Ac-DEVD-CHO
(ii) % Coefficient of Variance between Replicates: The % CV between replicates was within the acceptable limits (10%).

Example 12

Extract of *Lycopodium clavatum* Induces Morpholigcal Features Consistent with Apoptosis HeLa cells (cervical carcinoma) obtained from American Type Tissue Culture (ATCC) were treated for 48 hours with the extract from *Lycopodium Clavatum* and stained with anti-tubulin antibody to examine the cytoskeleton and nuclei were stained with 4',6-diamidino-2-phenylindole is a fluorescent stain that binds strongly to DNA (DAPI). Cells treated with vehicle revealed intact cytoplasmic structure and nuclei. While cells treated with the extract lost their cytoplasmic structure (rounded cells) and complete loss of nuclear DNA in cells as evidenced by loss of DNA appearing as empty space in nuclei. These morphological changes suggest that the BCP-21 induces apoptosis in cervical carcinoma cell line.

Example 13

Extract of *Lycopodium Clavatum* Induces Sub-G1 Population

Since the extract of *Lycopodium Clavatum* induces changes suggestive of apoptosis, apoptosis was evaluated by measuring DNA content using flow cytomery. The apoptotic cells loss DNA by fragmentation, hence would have DNA content less than 2n. On flow cytometry analysis, the cells would appear to run left of G1 peak and hence called 'sub-G1 peak'. HeLa cells treated with control and various dilutions (1:500) and 1:250 of the *Lycopodium Clavatum* extract were fixed in absolute ethanol and stained with propidium iodide for 30 mins with RNAse. The cells were analyzed at the core facility of Dana Farber Cancer Institute, Harvard Medical School (Boston, Mass.). MultiCycle software from Phoenix Flow Systems (San Diego, Calif.) will be used to deconvolute the cellular DNA content histograms to obtain quantitation of the percentage of cells in sub-G1 phase.

Figure 6:
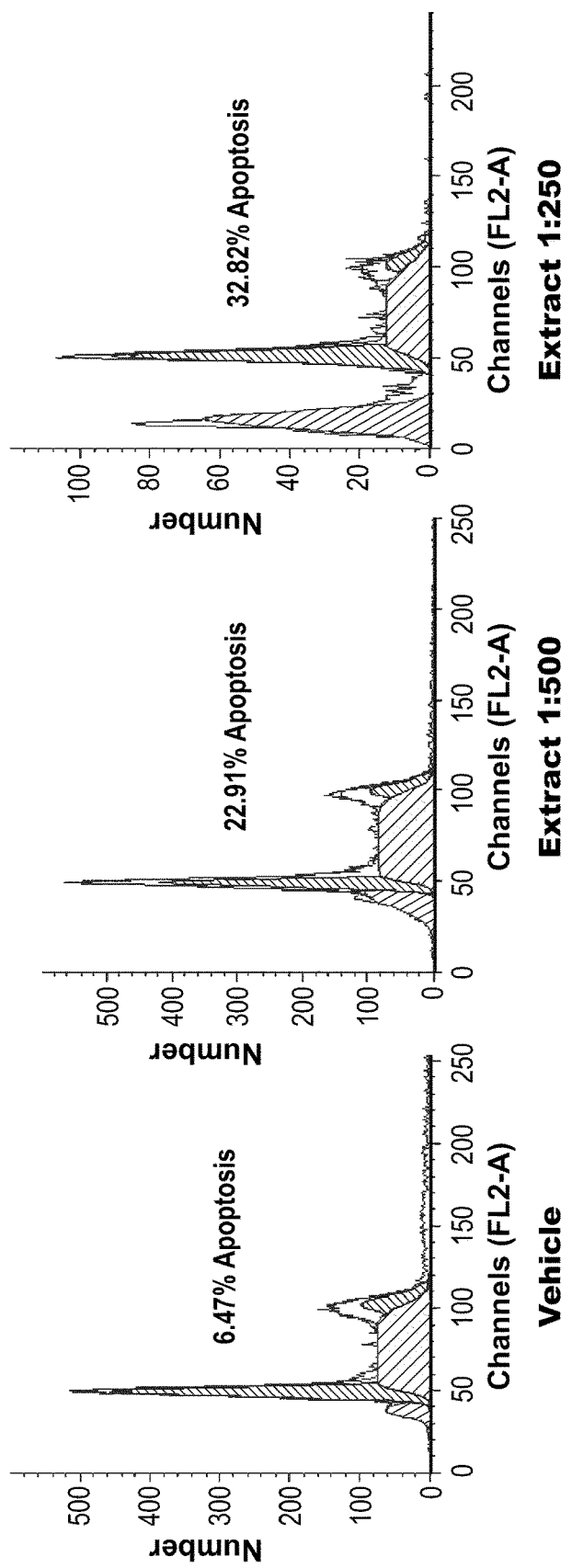
FIG. 6 shows that BCP-21 induces apoptosis of HeLa cells in a dose-dependent manner.

The crude extract of *Lycopodium Clavatum* increased sub-G1 peak (23%) compared to the control (6.7%) in a dose dependent manner (FIG. 6). The data strongly indicate that the extract induces apoptosis of HeLa cells in a dose-dependent manner.

Example 14

Extract of *Lycopodium Clavatum* Induces PARP Cleavage

Cells were lysed in 50 mM Tris-HCl, pH 7.6, 150 mM NaCl, 30 mM EDTA, 0.5% Triton X-100 with complete protease inhibitor (Roche). Protein samples were separated on an appropriate percentage of gel by SDS-PAGE. In general, 20-60 µg of protein were analyzed for endogenous proteins and 10-15 µg for transfected proteins. Protein was transferred to 0.2 µm nitrocellulose membrane (Bio-Rad) for 1 h at 4° C. for 1 h. Membranes were blocked for 45 minutes at room temperature (RT) in PBS solution containing 5% milk and 0.1% Tween-20 (American Bioanalytical. The nitrocellulose membrane was then incubated in primary antibody diluted at an appropriate concentration in PBS containing 1% milk and 0.1% Tween-20 for either 2 h at RT or overnight 4° C. Upon removal of the primary antibody, the membranes were washed 3 times for 10 minutes at RT in wash buffer (1×PBS with 1% milk and 0.1% Tween-20).

The membrane was then incubated for 1 h at RT in the appropriate secondary antibody diluted in wash buffer. Membrane was then washed for 3 times for 10 minutes. Western blot were developed using ECL (Pierce Laboratories) according to the manufacturer's instructions.

Figure 7:
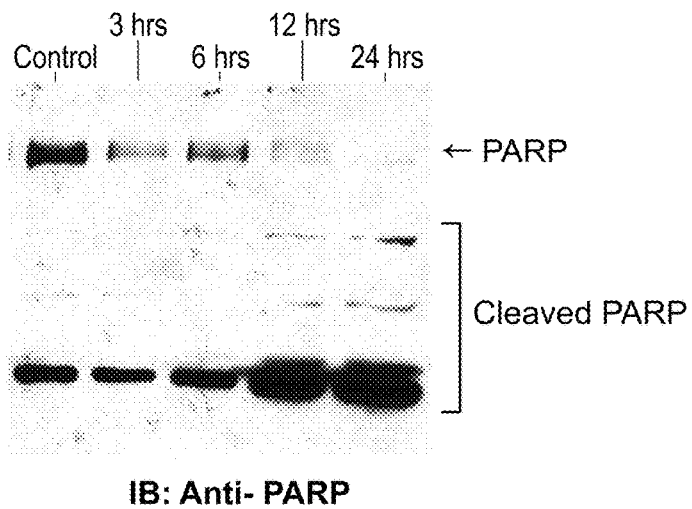
FIG. 7 is a western blotting result showing that the extract of *lycopodium clavatum* induces PARP cleavage in a time-dependent manner.

The result indicates that full length PARP (mol. wt. 116 kDa) was completely cleaved after 24 hours. HeLa cells treated with the extract show increase in PARP cleavage in a time-dependent manner (FIG. 7). This data strongly indicate that the Lycopodium extract induces apoptosis.

Example 15

Screening of Racemic Mixture of 8-HHA Against Human Tumor Cell Lines

The synthesized racemic mixture of 8-HHA dissolved in DMSO was accepted by the Division of Cancer Diagnosis and Treatment, National Cancer Institute, NIH for screening against 60 human tumor cell line panel. The screening is a microplate cytotoxicity assays based on a simple colorimetric (MTT) assay which relies on the metabolic reduction of a tetrazolium dye in viable cells to a colored formazan product. A modified protocol was used for the screening of the compound and measures the inhibition of growth of various tumor cell lines. The 8-HHA tested in this assay was at the concentration of 10 µM.

The result shows that 8-HHA has significantly suppressed the growth of leukemia cell lines (e.g., CCRF-CEM, K-562, SR, MOLT-4, RPMI-8226, and HL-60(TB)) ranging from 40-96%. It also demonstrated a remarkable inhibition of growth on non-small cell lung cancer cell lines (e.g, HOP-92, and NCI-H460). Also, three (i.e., HCT-116, HCT-15, and KM12) out of 7 colorectal cancer cell lines screened showed moderate evidence of growth suppression. This data indicates that 8-HHA has growth inhibitory activity against various cancer cell lines such as leukemia, lung and colorectal cancer cell lines, albeit to a variable extent.

Example 16

The Effects of 8-HHA on Survival of Cancer Cell Lines

1) Against the lung cancer cell lines: The effect of the racemic mixture of 8-HHA and that of the individual enantiomers, namely S and R enantiomers, were examined on the survival of HOP-92 lung cancer cell lines. The cell viability was examined in the exponential growth phase with 100 µM of 8-HHA for 72 hours using colorimetric MTT assay. In separate assays, HOP-92 cells were treated with different concentrations of the S-enantiomer of 8-HHA ranging from 20-100 µM for 72 hours.

Figure 8:
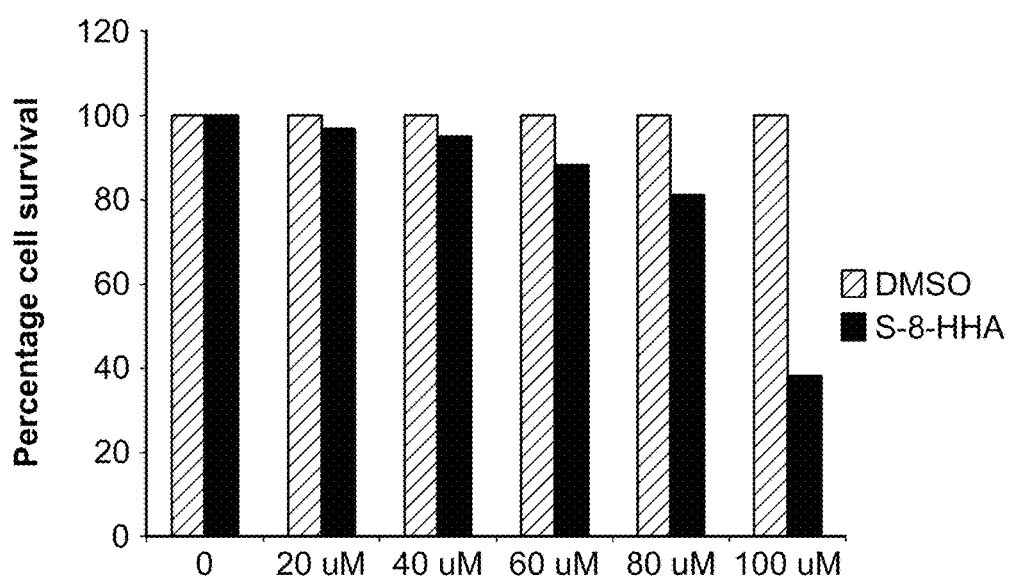
FIG. 8 shows that (S)-8-HHA inhibited HOP-92 lung cancer cell line survival in a dose dependent manner.

The results show that the racemic mixture of 8-HHA reduced the survival of HOP92 cell lines by 25%. The R-enantiomer reduced the survival of HOP92 cell lines by 13%. In contrast, the S-enantiomer had maximum effect on the survival of lung cancer cell line (reduced by 72%). This data indicate that S enantiomer of 8-HHA has a potent inhibitory effect on HOP92 lung cancer cell survival. Moreover, FIG. 8 shows that increasing concentrations of (S)-8-HHA inhibited lung cancer cell line survival in a dose dependent manner. A 50% reduction in cell survival ($IC_{50}$) was observed at approximately 90 µM dose of S-enantiomer of 8-HHA. This data strongly indicate that S enantiomer of 8-HHA has a dose-dependent inhibitory effect on lung cancer cell line.

2) Against the liver cancer cell lines: The effect of the racemic mixture of 8-HHA and that of the individual enantiomers, namely S and R enantiomers, were examined on survival of PLC/PRF/5 (also referred to as "PLC-5" or "PLC5"), Hep3B and SNU449 (also referred to as "SNU") liver cancer cell lines. The cell viability was examined in the exponential growth phase with 100 µM of 8-HHA for 72 hours using colorimetric MTT assay. In separate assays, PLC-5 cells were treated with different concentrations of S-enantiomer of 8-HHA ranging from 20-100 µM for 72 hours.

Figure 9:
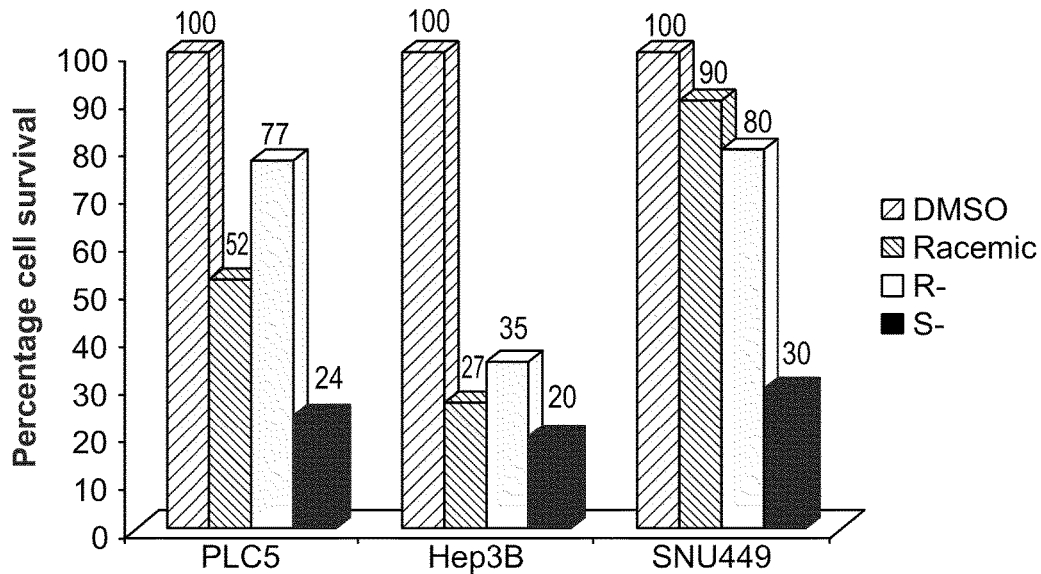
FIG. 9 shows that 100 μM of 8-HHA (the racemic mixture, S- or R-enantiomer) resulted in reduces survival of PCL5, Hep3B and SNU liver cancer cell lines using colorimetric MTT assay.

The results (FIG. 9) show that the racemic mixture of 8-HHA reduced the survival of PLC-5 and Hep3B cell lines by 52-25%, respectively. It had no major effect on SNU cell line. On the other hand, the S-enantiomer of 8-HHA had the maximum effect on the survival of all liver cancer cell lines (reduction of almost 75% cell survival) compared to either the racemic mixture or R-enantiomer. This data indicate that the S enantiomer of 8-HHA has a potent inhibitory effect on all of the liver cancer cell survival.

Figure 10:
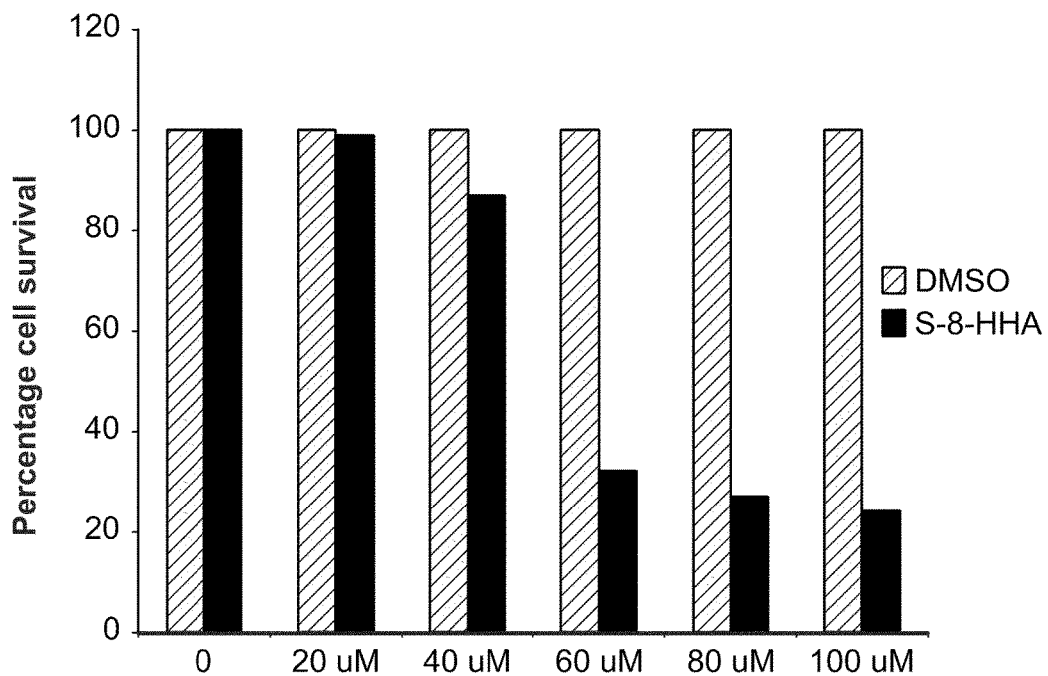
FIG. 10 demonstrates that (S)-8-HHA inhibited PLC-5 liver cancer cell line survival in a dose dependent manner.

Further, FIG. 10 demonstrates that increasing concentrations of (S)-8-HHA inhibited PLC-5 liver cancer cell line survival in a dose dependent manner. A 50% reduction in cell survival ($IC_{50}$) was observed at approximately 50 µM dose of S-enantiomer of 8-HHA This data strongly indicate that S enantiomer of 8-HHA has a dose-dependent inhibitory effect on lung cancer cell line.

Example 17

8-HHA Induces Apoptosis in Liver and Lung Cancer Cell Lines

PARP cleavage is considered a specific and well established marker of apoptosis. During apoptosis, FAS receptor undergoes down regulation, which is considered as an established indicator of apoptosis. Apoptosis can be induced by a pathway stimulated by FAS receptor binding to FAS ligand and is called extrinsic mechanism. Apoptosis by this pathway results in the reduction of FAS receptor. Therefore, a reduction in the protein levels of FAS receptor indicates that the apoptosis is induced by the extrinsic mechanism.

Figure 11:
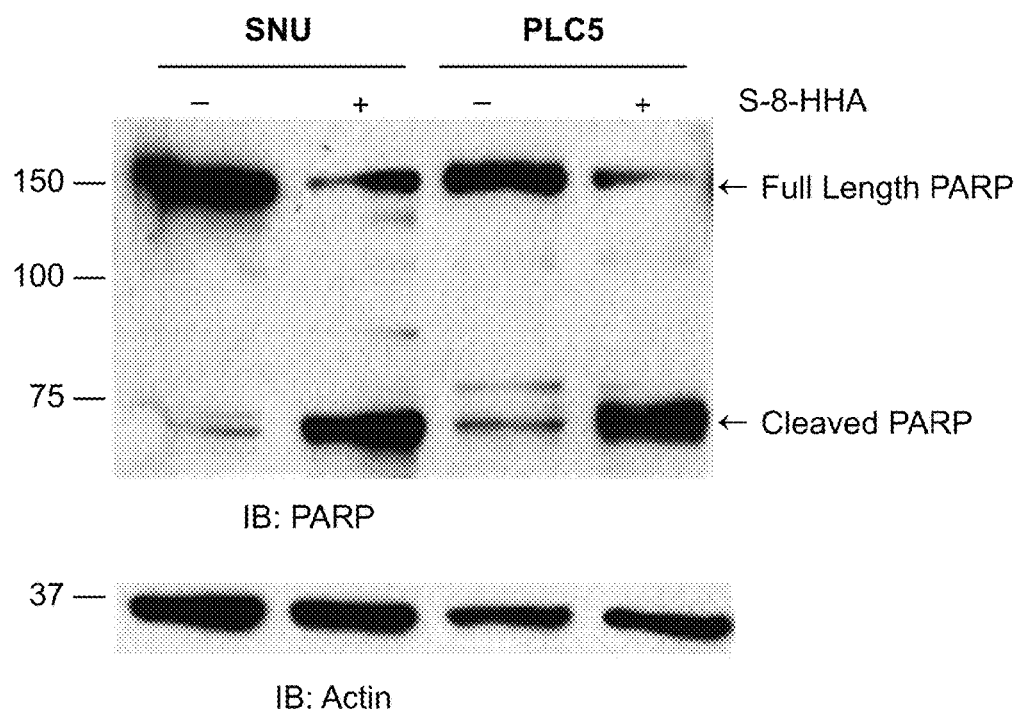
FIG. 11 shows that 100 μM of (S)-8-HHA resulted in the PARP cleavage in SNU and PCL5 liver cancer cell lines.

1) Against liver cancer cell lines: The effect of 8-HHA was examined on apoptosis in liver cancer cell lines. FIG. 11 shows that the treatment of 100 µM of the S-enantiomer of 8-HHA resulted in the PARP cleavage in SNU and PLC-5 liver cancer cell lines. This data indicate that 8-HHA induces apoptosis in liver cancer cell line.

Figure 12:
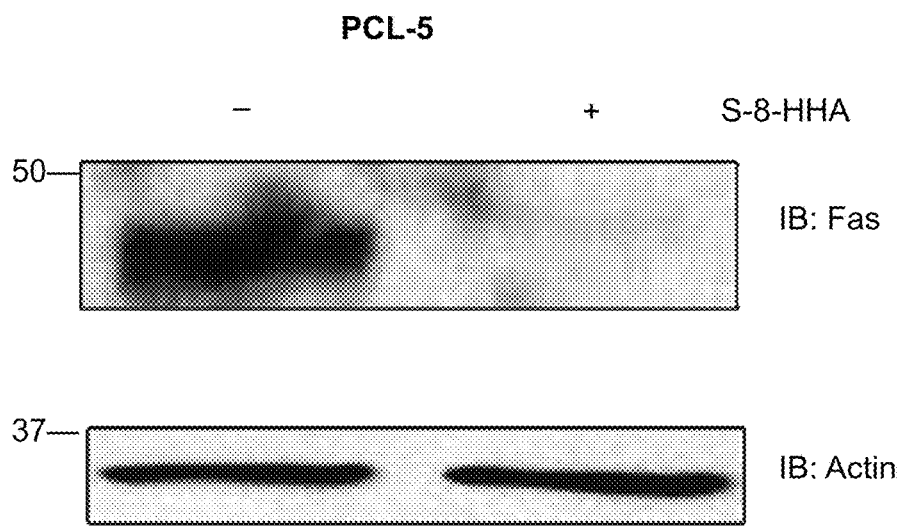
FIG. 12 demonstrates that a treatment of (S)-8-HHA resulted in a substantial reduction in FAS receptor levels compared to the control.

PLC-5 cell lines were treated with 100 8-HHA of 100 µM for 72 hours. This resulted in a substantial reduction in FAS receptor levels with the treatment of (S)-8-HHA compared to the control (FIG. 12). This data suggests that (S)-8-HHA induces apoptosis in liver cancer cell line by the extrinsic pathway.

2) Against lung cancer cell lines: HOP-92 lung cancer cell lines were treated with 100 µM of (S)-8-HHA for 72 hours. The (S)-8-HHA treatment resulted in the reduction of FAS protein levels in HOP92 cell lines. This data indicates that 8-HHA induces apoptosis in HOP92 cell lines through extrinsic mechanism.

Example 18

The Effect of 8-HHA Treatment on Pro-Apoptotic Bim1 in Lung Cancer Cell Line

Bim1 is a pro-apoptotic protein whose up regulation leads to apoptosis. HOP92 cell lines were treated with 100 µM of S-enantiomer of 8-HHA for 72 hours. The results show that Bim1 increased by 2 fold in 8-HHA treated compared to the control sample. This data indicate that 8-HHA induces apoptosis in lung cancer cell lines.

Example 19

Determination of Maximal Tolerated Dose (MTD) of 8-HHA for an In Vivo Animal Model The purpose of this study was to determine the maximum tolerated dose of 8-HHA following intravenous (IV) administration in ICR mice. A racemic mixture of 8-HHA, placebo, and vehicle were administered to 20 ICR female mice with weight of 25-30 grams, respectively. The 8-HHA was formulated in nanolipid at concentration of 0, 10, 20 and 40 mg/ml. There were 4 animals per group and they were injected with 0, 10, 20 and 40 mg/kg dose of 8-HHA Mice were given a single bolus dose via the tail vein according to group assignment. One week after dosing mice were sacrificed. Daily clinical observations were performed 15 minutes and 1 hour post dose. The mice were observed daily for any adverse effects until necropsy on study day 8. Body weights were recorded for all the mice prior to test substance administration, and every other day throughout the test period. This entire study was performed at Toxikon Corporation, Bedford, Mass. The results are depicted in Table 6.

TABLE 6

| Group | Test Articles | | Dose | | | |
| | Placebo (mg/kg) | 8-HHA (mg/kg) | Concentration | Route | Volume (mL/kg) | Number of animals |
|---|---|---|---|---|---|---|
| 1 | 0 | 0 | 0 | IV | 2 | 4 per group |
| 2 | 0 | 10 | 5 | | | |
| 3 | 0 | 20 | 10 | | | |
| 4 | 0 | 40 | 20 | | | |

Results and discussions: Body weight at day 6 and 8 did not vary from pre dose weight. Body weight at day 6 and 8 did not vary from pre dose weight. Two mice dosed with the high dose (40 mg/kg) died shortly after being dosed. Animals dosed with placebo, 10 mg/kg and 20 mg/kg tolerated the 8 HHA well and did not demonstrate any clinical abnormalities to be noted. The dose of 20 mg/kg was then considered as maximum tolerated dose of 8-HHA Example 20

Liver Xenograft Mouse Model

The purpose of this study was to determine anti tumor efficacy of 8-HHA in liver cancer using PLC5 cells a Hepatocellular Carcinoma cell line. The tumor growth and animal survival were considered as primary end point.

Animals and care: Thirty BABL/c nude, non-pregnant and nulliparous female mice that are 5-6 weeks old and weighing 16-20 gms were used in this study. BALB/c nu/nu mice were used because they have been historically used in xenograft studies to test anti-tumor efficacy of drug candidates. Mice were acclimatized for minimum 5 days, under same conditions as for the actual test. Mice were housed at room temperature 68±5° F. with room Relative Humidity of 30-70%, air Exchanges per Hour of a minimum of 10 changes per hour, lights exposure of 12-hour light/dark cycle, full spectrum fluorescent lights. The mice were housed in groups in ventilated micro-isolator cages made up of polycarbonate. The mice were using autoclaved laboratory grade bedding and were provided ad libitum with irradiated pellets and autoclaved water. There were no known contaminants present in the feed, water, or bedding expected to interfere with the test data. The laboratory and animal rooms were maintained as limited-access facilities.

Route of injection and dose: 8-HHA was administered through intraperitoneal (IP) injection. 8-HHA is poorly water soluble, hence suspended in nanolipid dispersion solution (ePharse, Basel, Switzerland) at the concentration of 27.2 mg/ml corresponding to 100 mM. The MTD assay (Preliminary data) showed that the mice tolerated a maximum dose of 20 mg/kg. For this study, 2 doses-10 mg/kg and 100 mg/kg were used.

Animal Preparation

Tumor Induction: The cell line PLC5 were cultured according to recommended specifications at Vanas Oncology, in which cells were grown and maintained in RPMI medium containing 10% fetal bovine serum, 2 mM L-Glutamine, 100 units/ml of Streptomycin and 100 units/ml of Penicilin. Cells were trypizinized and counted using the Trypan-blue viability test using a hemocytometer. Cell counts in quadrants of the hemocytometer were converted to a cells/mL value, which will enable isolation of the appropriate number of cells per mouse. Each mouse was inoculated subcutaneously in the right flank region with 0.2 mL of a 50% RPMI/50% Matrigel™ mixture containing a suspension of tumor cells ($5 \times 10^6$ cells/mouse). Tumors were observed twice weekly until well established. Tumor volume was calculated using the formula: Tumor weight (mg)=(a× $b^2$/2) where 'b' is the smallest diameter and 'a' is the largest diameter in millimeters.

Allocation of Animals: Once the established tumors reach a mean calculated volume of approximately 50-100 mg, the mice were randomized, using appropriate software, into treatment groups in order to reduce the variability of tumor sizes per group.

Pre Dose Procedure: Acclimated animals were weighed and observed for clinical signs of toxicity prior to dosing on Day 1.

Dose Administration Two doses 1 and 10 mg/kg were administered based on the MTD assay guideline. The first day of dosing is Day 1. On Day 1,8-HHA, and vehicle injections were administered according to the study design in Table 7 below.

TABLE 7

Study Design

| Model | Groups | Number of Animals | Treatment | Route | Dosage | Duration of Treatment |
|---|---|---|---|---|---|---|
| Hepatocellular carcinoma model | C1 | 10 | Control | IP | NA | Five days a week for 3 weeks |
| | T1 | 10 | 8-HHA | | 10 mg/kg | |
| | T2 | 10 | 8-HHA | | 100 mg/kg | |

Post Dose Procedure: Following treatment, tumor and mouse body weight measurements were recorded twice weekly and gross observation was made at least once daily. Mice with tumors that are not palpable was considered complete regressions. Percentage of mice mortality and time of death will be recorded for every group in the study. Animals may be defined as moribund and sacrificed if one or more of the following criteria are met:

Loss of body weight of 20% or greater in a 1 week period.
Mice that inhibit normal physiological function such as eating, drinking, mobility, and ability to urinate and/or defecate.
Tumors that exceed a maximum size of 2000 mg as measured by calipers.
Ulcerated tumors, or tumors that bleed or produce exudates.
Prolonged, excessive diarrhea leading to excessive weight loss (>20%).
Persistent wheezing and respiratory distress.
Prolonged or excessive pain or distress as defined by clinical observations such as: prostration, hunched posture, paralysis/paresis, distended abdomen, ulcerations, abscesses, seizures, and/or hemorrhages.

After completion of dosing, mice were observed for additional two weeks to check for regrowth of tumors.

Sacrifice: All animals will be sacrificed at the termination of the study, and the tumor will be harvested. One portion of the tumor will be frozen in OCT solution and the other portion will be fixed in formalin. The frozen and fixed tissues will be sent to the Sponsor.

All the animal experiments were performed at Toxikon Corporation (Bedford, Mass.).

Figure 13:
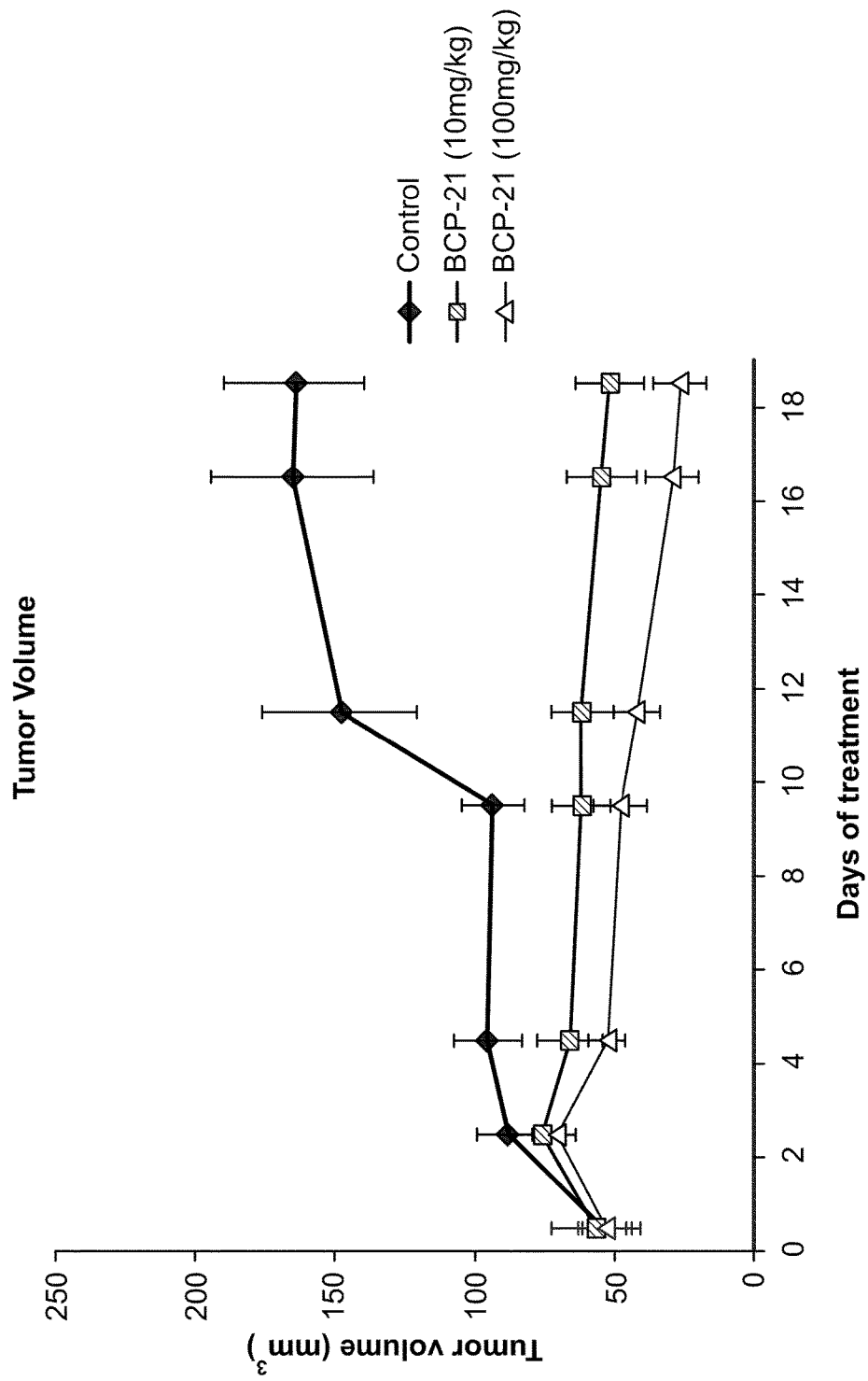
FIG. 13 depicts that 8-HHA decreases tumor growth in PLC5 liver cancer cells in liver xenograft mouse model.

Results: On day 1 of 8-HHA treatment, mice were randomly divided into three groups with 10 mice per group: control group vehicle only (C1), 8-HHA 10 mg/Kg body weight (T1) and 100 mg/Kg body weight (T2). Both the group T1 and T2 significantly inhibited tumor growth in mice from day 4 of 8-HHA treatment. In contrast, in the 8-HHA treated group (T1), the tumor volumes were decreased by 44.5%, 49.8%, 72.3%, 77.7% and 78.4% 9 (on days 4, 9, 11, 16 and 18, respectively) compared to the control group. In the T2 group, the tumor volumes were decreased by 56.3%, 61.1%, 81.1%, 87.9% and 88.3% (on days 4, 9, 11, 16 and 18, respectively) (see FIG. 13 and Table 8).

These results show that the two concentrations of 8-HHA used in this study decreases tumor growth in the liver cancer mouse model, by anti-proliferative and pro-apoptotic effects as evidenced from our in vitro experiments using PLC-5 cells. 8-HHA may thus prove to be a very effective, safe, and inexpensive adjunct to standard chemotherapy regimens.
(*S: Significant compared to control group; N=10/group)
Mean±SEM Tumor Volume (PLC-5)

Example 21

Small Cell Lung Cancer Xenograft Mouse Model

The purpose of this study was to determine anti tumor efficacy of 8-HHA in lung cancer using HOP92 cells.

Animals and care: Thirty BABL/c nude, non-pregnant and nulliparous female mice that are 5-6 weeks old and weighing 16-20 gms were used in this study. BALB/c nu/nu mice were used because they have been historically used in xenograft studies to test anti-tumor efficacy of drug candidates. Mice were acclimatized for minimum 5 days, under same conditions as for the actual test. Mice were housed at room temperature 68±5° F. with room Relative Humidity of 30-70%, air Exchanges per Hour of a minimum of 10 changes per hour, lights exposure of 12-hour light/dark cycle, full spectrum fluorescent lights. The mice were housed in groups in ventilated micro-isolator cages made up of polycarbonate. The mice were using autoclaved laboratory grade bedding and were provided ad libitum with irradiated pellets and autoclaved water. There were no known contaminants present in the feed, water, or bedding expected to interfere with the test data. The laboratory and animal rooms were maintained as limited-access facilities.

Route of injection and dose: 8-HHA was administered through intraperitoneal (IP) injection. 8-HHA is poorly water soluble, hence suspended in nanolipid dispersion solution (ePharse, Basel, Switzerland) at the concentration of 27.2 mg/ml corresponding to 100 mM. The MTD assay (Preliminary data) showed that the mice tolerated a maximum dose of 20 mg/kg.

Experimental Design:

Animal Preparation

Tumor Induction: The cell line HOP92 were cultured according to recommended specifications at Vanas Oncology as above discussed in Example 20. Cells were trypizinized and counted using the Trypan-blue viability test using a hemocytometer. Cell counts in quadrants of the hemocytometer were converted to a cells/mL value, which will enable isolation of the appropriate number of cells per mouse. Each mouse was inoculated subcutaneously in the right flank region with 0.2 mL of a 50% RPMI/50% Matrigel™ mixture containing a suspension of tumor cells ($5\times10^6$ cells/mouse). Tumors were observed twice weekly until well established. Tumor volume was calculated using the formula: Tumor weight (mg)=$(a\times b^2/2)$ where 'b' is the smallest diameter and 'a' is the largest diameter in millimeters.

Allocation of Animals: Once the established tumors reach a mean calculated volume of approximately 50-100 mg, the

TABLE 8

| Groups | Randomization (Pre-Dose) | Day 2 | Day 4 | Day 9 | Day 11 | Day 16 | Day 18 |
|---|---|---|---|---|---|---|---|
| Control | 53.81 ± 7.90 | 88.57 ± 10.52 | 95.40 ± 12.06 | 93.71 ± 11.19 | 148.3 ± 27.75 | 165.3 ± 28.92 | 164.6 ± 25.02 |
| BCP-21 10 mg/kg | 56.73 ± 16.11 | 76.17 ± 12.01 | 66.21 ± 11.71 | 61.85 ± 10.29* | 61.89 ± 10.97* | 54.46 ± 12.65* | 51.91 ± 12.42* |
| BCP-21 100 mg/kg | 53.42 ± 9.56 | 71.42 ± 8.10 | 52.91 ± 6.7* | 47.97 ± 9.59* | 42.22 ± 8.25* | 29.52 ± 9.30* | 26.69 ± 9.39* |
| Statistical Significance | NS P > 0.05 | NS P > 0.05 | *S P < 0.05 | *S P < 0.05 | *S P < 0.05 | *S P < 0.05 | *S P < 0.05 | mice were randomized, using appropriate software, into treatment groups in order to reduce the variability of tumor sizes per group.

Pre Dose Procedure: Acclimated animals were weighed and observed for clinical signs of toxicity prior to dosing on Day 1.

Dose Administration Two doses 1 and 10 mg/kg were administered. The first day of dosing is Day 1. On Day 1,8-HHA, and vehicle injections are administered according to the study design in Table 9 below.

TABLE 9

Study Design

| Model | Groups | Number of Animals | Treatment | Route | Dosage | Duration of Treatment |
|---|---|---|---|---|---|---|
| Non-Small cell lung cancer | C1 | 10 | Control | IP | NA | Five days a week for 3 weeks |
| | T1 | 10 | 8-HHA | | 10 mg/kg | |
| | T2 | 10 | 8-HHA | | 100 mg/kg | |

Post Dose Procedure: Following treatment, tumor and mouse body weight measurements were recorded twice weekly and gross observation was made at least once daily. Mice with tumors that were not palpable was considered complete regressions. Percentage of mice mortality and time of death were recorded for every group in the study. Animals may be defined as moribund and sacrificed if one or more of the following criteria are met:

Loss of body weight of 20% or greater in a 1 week period.
Mice that inhibit normal physiological function such as eating, drinking, mobility, and ability to urinate and/or defecate.
Tumors that exceed a maximum size of 2000 mg as measured by calipers.
Ulcerated tumors, or tumors that bleed or produce exudates.
Prolonged, excessive diarrhea leading to excessive weight loss (>20%).
Persistent wheezing and respiratory distress.
Prolonged or excessive pain or distress as defined by clinical observations such as: prostration, hunched posture, paralysis/paresis, distended abdomen, ulcerations, abscesses, seizures, and/or hemorrhages.

After completion of dosing, mice were observed for additional two weeks to check for regrowth of tumors.

Sacrifice: All animals will be sacrificed at the termination of the study, and the tumor will be harvested. One portion of the tumor will be frozen in OCT solution and the other portion will be fixed in formalin. The frozen and fixed tissues were sent to the Sponsor.

Figure 14:
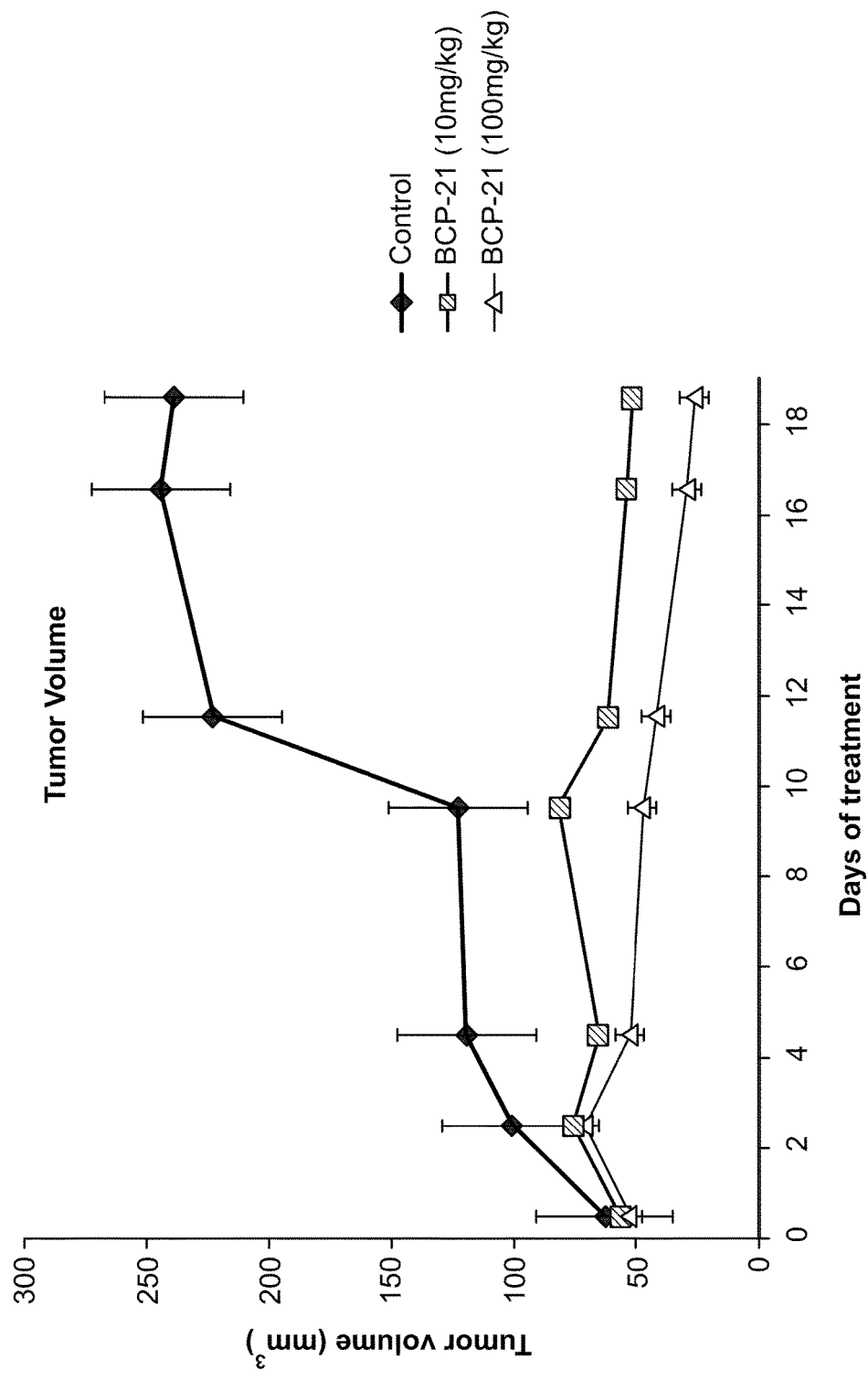
FIG. 14 depicts anti-tumor efficacy of 8-HHA in HOP92 lung cancer cells in xenograft mouse model.

Results: On day 1 of 8-HHA treatment, mice were randomly divided into three groups with 10 mice per group: control group vehicle only (C1), 8-HHA 10 mg/Kg body weight (T1) and 100 mg/Kg body weight (T2). Both the group T1 and T2 significantly inhibited tumor growth in mice from day 16 of 8-HHA treatment. The tumor volumes were 214.6±38.65, and 258.4.±64.96 mm$^3$ on days 16 and 18, respectively, in the control group. In contrast, in the 8-HHA treated group (T1), the tumor volumes were 88.78±28.61 and 82.02±25.93 mm$^3$ on days 16 and 18, respectively, corresponding to 58.6%, and 68.2% decreases in tumor 32.63 mm$^3$ on days 16 and 18, respectively, corresponding to 56.5%, and 73.1% decreases in tumor volume (see Table 10 and FIG. 14)

TABLE 10

| Groups | Randomization (Pre-Dose) | Day 2 | Day 4 | Day 9 | Day 11 | Day 16 | Day 18 |
|---|---|---|---|---|---|---|---|
| Control | 87.18 ± 28.73 | 120.7 ± 30.09 | 169.4 ± 56.48 | 174.6 ± 35.93 | 189.1 ± 34.53 | 214.6 ± 38.65 | 258.4 ± 64.96 |
| BCP-21 10 mg/kg | 89.64 ± 30.12 | 128.9 ± 32.45 | 116.0 ± 39.22 | 99.92 ± 32.57 | 94.31 ± 30.19 | 88.78 ± 28.61* | 82.08 ± 25.93* |
| BCP-21 100 mg/kg | 86.68 ± 14.32 | 141.6 ± 31.42 | 120.7 ± 26.45 | 106.1 ± 25.47 | 105.3 ± 29.05 | 93.38 ± 30.46* | 91.27 ± 32.63* |
| Statistical Significance | NS P > 0.05 | NS P > 0.05 | NS P > 0.05 | NS P > 0.05 | NS P > 0.05 | *S P < 0.05 | *S P < 0.05 |

*S: Significant compared to control group
Mean ± SEM Tumor Volume (HOP-92) (N = 10/group)

In conclusion, the two concentrations of 8-HHA used in this study decreased tumor growth in the lung cancer mouse model, by anti-proliferative and pro-apoptotic effects as evidenced from our in vitro experiments using HOP92 cells. 8-HHA may thus prove to be a very effective, safe, and inexpensive adjunct to standard chemotherapy regimens.

Although the invention has been disclosed with reference to specific embodiments, it is apparent that other embodiments and variations of the invention may be devised by others skilled in the art without departing from the true spirit and scope of the invention.

What is claimed is:

1. A method of treating cancer in a subject comprising administering to the subject a composition comprising an effective amount of 8-hydroxyhexadecanoic acid, or a salt thereof, thereby treating said cancer;
   wherein said cancer is a lung cancer.

2. A method of treating cancer in a subject comprising administering to the subject a composition comprising an effective amount of 8-hydroxyhexadecanoic acid, or a salt thereof, thereby treating said cancer;
   wherein said cancer is a lung cancer;
   wherein said lung cancer is a non-small cell lung cancer.

3. A method of treating cancer in a subject comprising administering to the subject a composition comprising an effective amount of 8-hydroxyhexadecanoic acid, or a salt thereof, thereby treating said cancer;

wherein said cancer is a lung cancer;
wherein said lung cancer is mediated by HOP-92 or NCI-H460 cancer cells.

4. A method of treating cancer in a subject comprising administering to the subject a composition comprising an effective amount of 8-hydroxyhexadecanoic acid, or a salt thereof, thereby treating said cancer;
wherein said cancer is leukemia.

5. A method of treating cancer in a subject comprising administering to the subject a composition comprising an effective amount of 8-hydroxyhexadecanoic acid, or a salt thereof, thereby treating said cancer;
wherein said cancer is leukemia;
wherein said leukemia is mediated by CCRF-CEM, K-562, SR, MOLT-4, RPMI-8226, or HL-60(TB) cancer cells.

* * * * *